US006348200B1

(12) United States Patent
Nakajima et al.

(10) Patent No.: US 6,348,200 B1
(45) Date of Patent: Feb. 19, 2002

(54) COSMETIC COMPOSITION

(75) Inventors: Atsushi Nakajima; Masataka Fukuda; Takeshi Morita; Toshio Uesaka; Tomoko Sadahiro, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 08/849,250

(22) PCT Filed: Oct. 15, 1996

(86) PCT No.: PCT/JP96/02982

§ 371 Date: Jun. 16, 1997

§ 102(e) Date: Jun. 16, 1997

(87) PCT Pub. No.: WO97/14401

PCT Pub. Date: Apr. 24, 1997

(30) Foreign Application Priority Data

Oct. 16, 1995 (JP) .............................. 7-267422
Dec. 15, 1995 (JP) .............................. 7-327224
Jan. 30, 1996 (JP) .............................. 8-013917

(51) Int. Cl.⁷ .............................. A61K 6/00; A61K 7/00
(52) U.S. Cl. .................. 424/401; 424/195.1; 424/70.1; 424/70.17
(58) Field of Search ............................... 424/401, 70.1, 424/70.17; 514/788, 847, 844

(56) References Cited

U.S. PATENT DOCUMENTS 4,021,539 A  * 5/1977 Moller et al. .................. 424/73
5,552,445 A    9/1996 Ohashi et al.
5,641,495 A  * 6/1997 Jokura et al. ............... 424/401
5,681,864 A   10/1997 Ohashi et al.

FOREIGN PATENT DOCUMENTS

EP   0282816 A   * 9/1988
FR   2358138     * 2/1978
JP   88-266512   * 8/1988
JP   408225428 A * 9/1996
WO   WO 94/23694 * 10/1994

* cited by examiner

*Primary Examiner*—Thurman K. Page
*Assistant Examiner*—Liliana Di Nola-Baron
(74) *Attorney, Agent, or Firm*—Oblon, Spviak, McClelland, Maier & Neustadt, P.C.

(57) ABSTRACT

The present invention relates to cosmetic compositions comprising (A) at least one amide derivative having a specified formula; and (B) at least one ingredient selected from the group consisting of (B-1) polyhydric alcohols, (B-2) vegetable extracts and (B-3) organic acids or salts thereof. The compositions can enhance the water-retaining ability of the horny layer and have excellent effects for improving skin roughness and preventing the formation of wrinkles.

21 Claims, No Drawings

COSMETIC COMPOSITION

BACKGROUND OF THE INVENTION

1. Field of the Invention

The present invention relates to cosmetic compositions which can enhance the water-retaining ability of the horny layer and have excellent effects in improving skin roughness and preventing the formation of wrinkles.

2. Discussion of the Background

The water content of the horny layer has heretofore been known to be critical for imparting moisture to the skin to maintain skin smoothness and softness. The retention of water in the horny layer is said to rely upon a water-soluble component contained in the horny layer, namely, a free amino acid, organic acid, urea or inorganic ion.

In the above circumstances, these materials have been incorporated either singly or in combination in cosmetics and the like with a view toward improving or preventing skin roughness.

Besides, many humectants having a high affinity for water have also been developed and have been used for improving the skin roughness.

However, these humectants remain on the skin surface when they are applied to the skin, so that they serve to supply water to the horny layer. Moreover, their effects are temporary and they are not such that can fundamentally improve the water-retaining ability of the horny layer itself and can prevent or cure skin roughness substantially.

Therefore, the present applicant previously proposed, as an external skin care composition having the effect of fundamentally improving the water-retaining ability of the horny layer, an external skin care composition [Japanese Patent Publication No. 42934/1989 (Japanese Patent Application Laid-Open No. 228048/1987)] comprising an amide derivative represented by the following formula (a):

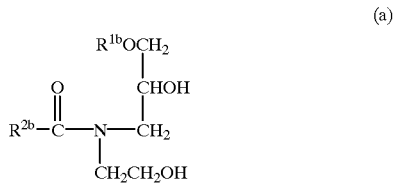

(a)

wherein $R^{1b}$ is a linear or branched and saturated or unsaturated hydrocarbon group having 10–26 carbon atoms, and $R^{2b}$ is a linear or branched and saturated or unsaturated hydrocarbon group having 9–25 carbon atoms.

Further, the present applicant proposed external skin care compositions having the same effects as described above in Japanese Patent Application Laid-Open Nos. 216812/1988, 218609/1988, 222107/1988, 227513/1988, 29347/1989, and 31752/1989, etc.

However, the amide derivatives used in these external skin care compositions bring about the excellent effects as described above, but have such properties as high melting point, high crystallinity and low solubility in a base, and so they still involve problems to be solved from the viewpoint of penetration into the skin, and the like when incorporated into cosmetics. There has thus remained a demand for development of a cosmetic composition having excellent effects in improving skin roughness.

SUMMARY OF THE INVENTION

It is therefore an object of the present invention to provide novel cosmetic compositions which have the effect of fundamentally improving (maintaining or enhancing) the water-retaining ability of the horny layer.

It is another object of the present invention to provide novel cosmetic compositions which can prevent and cure skin roughness or inflammation, and moreover can prevent dermal aging such as the formation of wrinkles to enhance the protective and maintenance performance of the skin.

These and other objects, which will become apparent from the following detailed description, have been achieved by the inventors' discovery that cosmetic compositions comprising at least one compound selected from novel amide derivatives represented by the general formulae (1) to (4), which will be described subsequently, and at least one ingredient selected from polyhydric alcohols, vegetable extracts and organic acids or salts thereof can achieve the above object, thus leading to completion of the present invention.

According to the present invention, there is thus provided a cosmetic composition comprising the following components (A) and (B):

(A) at least one compound selected from the amide derivatives represented by the following general formulae (1), (2), (3) and (4):

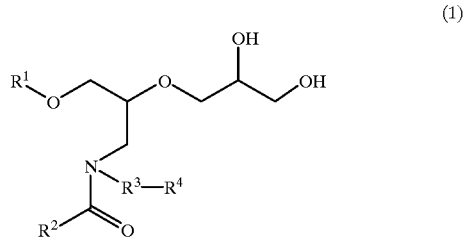

(1)

wherein $R^1$ and $R^2$ are identical to or different from each other and are, independently, a hydrocarbon group having 1 to 40 carbon atoms, which may be hydroxylated, $R^3$ is a linear or branched alkylene group having 1 to 6 carbon atoms, or a single bond, and $R^4$ is a hydrogen atom, a linear or branched alkoxyl group having 1 to 12 carbon atoms, or a 2,3-dihydroxypropyloxy group, with the proviso that when $R^3$ is a single bond, $R^4$ is a hydrogen atom;

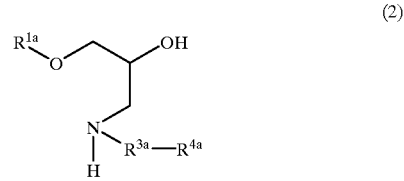

(2)

wherein $R^{1a}$ is a hydrocarbon group having 4 to 40 carbon atoms, which may be hydroxylated, $R^{3a}$ is a linear or branched alkylene group having 3 to 6 carbon atoms, and $R^{4a}$ is a linear or branched alkoxyl group having 1 to 12 carbon atoms,

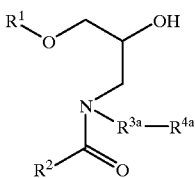

(2)

wherein $R^1$ and $R^2$ are identical to or different from each other and are, independently, a hydrocarbon group having 1 to 40 carbon atoms, which may be hydroxylated, $R^{3a}$ is a linear or branched alkylene group having 3 to 6 carbon atoms, and $R^{4a}$ is a linear or branched alkoxyl group having 1 to 12 carbon atoms;

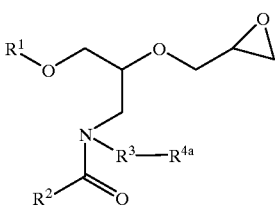

(2)

wherein $R^1$ and $R^2$ are identical to or different from each other and are, independently, a hydrocarbon group having 1 to 40 carbon atoms, which may be hydroxylated, $R^3$ is a linear or branched alkylene group having 1 to 6 carbon atoms, or a single bond, and $R^{4b}$ is a hydrogen atom, a linear or branched alkoxyl group having 1 to 12 carbon atoms, or a 2,3-epoxypropyloxy group, with the proviso that when $R^3$ is a single bond, $R^{4b}$ is a hydrogen atom; and (B) at least one component selected from the group consisting of (B-1) polyhydric alcohols, (B-2) vegetable extracts and (B-3) organic acids or salts thereof.

DETAILED DESCRIPTION OF THE PREFERRED EMBODIMENTS

In the amide derivative (1) represented by the general formula (1) of the component (A) useful in the practice of the present invention, $R^1$ and $R^2$ are identical to or different from each other and are, independently, a linear or branched and saturated or unsaturated hydrocarbon group having 1 to 40 carbon atoms, which may be hydroxylated. Examples of $R^1$ and $R^2$ include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, heneicosyl, docosyl, nonacosyl, triacontyl, isostearyl, isoheptadecyl, 2-ethylhexyl, 1-ethylheptyl, 8-heptadecyl, 8-heptadecenyl, 8,11-heptadecadienyl, 2-heptylundecyl, 9-octadecenyl, 1-hydroxynonyl, 1-hydroxypentadecyl, 2-hydroxypentadecyl, 15-hydroxypentadecyl, 11-hydroxyheptadecyl, and 11-hydroxy-8-heptadecenyl.

As $R^1$, linear or branched alkyl or alkenyl groups having 8 to 26 carbon atoms are preferred. Examples thereof include octyl, decyl, dodecyl, tetradecyl, hexadecyl, octadecyl, docosyl, triacontyl, isostearyl, 2-ethylhexyl, 2-heptylundecyl, and 9-octadecenyl. Linear or branched alkyl groups having 12 to 22 carbon atoms are particularly preferred hydrocarbon groups as $R^1$. Examples thereof include dodecyl, tetradecyl, hexadecyl, octadecyl, docosyl, and methyl-branched isostearyl groups.

As $R^2$, linear or branched alkyl or alkenyl groups having 9 to 25 carbon atoms are preferred. Examples thereof include nonyl, undecyl, tridecyl, tetradecyl, pentadecyl, heptadecyl, heneicosyl, nonacosyl, isoheptadecyl, 1-ethylheptyl, 8-heptadecyl, 8-heptadecenyl, 8,11-heptadecadienyl, 1-hydroxynonyl, 1-hydroxypentadecyl, 2-hydroxypentadecyl, 15-hydroxypentadecyl, 11-hydroxyheptadecyl, and 11-hydroxy-8-heptadecenyl. Linear or branched alkyl groups having 11 to 21 carbon atoms are particularly preferred hydrocarbon groups as $R^2$. Examples thereof include undecyl, tridecyl, tetradecyl, pentadecyl, heptadecyl, heneicosyl, and methyl-branched isoheptadecyl groups.

$R^3$ is a linear or branched alkylene group having 1 to 6 carbon atoms, or a single bond. Examples of the alkylene group include methylene, ethylene, trimethylene, tetramethylene, pentamethylene, hexamethylene, 1-methylethylene, 1-methyltrimethylene, 2-methyltrimethylene, 1,1-dimethylethylene, 1-ethylethylene, 1-methyltetramethylene, and 2-ethyltrimethylene. As $R^3$, linear alkylene groups having 1 to 6 carbon atoms are preferred with methylene, ethylene, and trimethylene groups being particularly preferred.

$R^4$ is a hydrogen atom, a linear or branched alkoxyl group having 1 to 12 carbon atoms, or a 2,3-dihydroxypropyloxy group. Examples of the alkoxyl group include methoxy, ethoxy, propoxy, butoxy, hexyloxy, octyloxy, decyloxy, 1-methylethoxy and 2-ethylhexyloxy. As $R^4$, a hydrogen atom, alkoxy groups having 1 to 8 carbon atoms and a 2,3-dihydroxypropyloxy group are preferred with a hydrogen atom, and methoxy, ethoxy, propoxy, butoxy, 1-methylethoxy, 2-ethylhexyloxy, and 2,3-dihydroxypropyloxy groups being particularly preferred.

Of the amide derivatives (1), particularly preferred are compounds in which $R^1$, $R^2$, $R^3$, and $R^4$ in the general formula (1) are groups respectively selected from the particularly preferred groups respectively mentioned above.

In the amide derivative (2) represented by the general formula (2) of the component (A) useful in the practice of the present invention, examples of $R^{1a}$ include the same groups as those in $R^1$ of the amide derivative (1) except that methyl, ethyl and propyl are excluded. Preferred groups are the same groups as those in $R^1$. Examples of $R^{3a}$ include the alkylene groups exemplified as $R^3$ of the amide derivative (1) except that methylene and ethylene are excluded. Preferred groups are the same as those in $R^3$. As $R^{3a}$, linear alkylene groups having 3 to 6 carbon atoms are preferred with trimethylene being particularly preferred. Examples of the alkoxyl group represented by $R^{4a}$ include the same groups as those in $R^4$ of the amide derivative (1). Preferred groups are the same groups as those in $R^4$.

Of the amide derivatives (2), particularly preferred are compounds in which $R^{1a}$, $R^{3a}$ and $R^{4a}$ in the general formula (2) are groups respectively selected from the particularly preferred groups respectively mentioned above.

In the amide derivative (3) represented by the general formula (3) of the component (A) useful in the practice of the present invention, $R^1$, $R^2$, $R^{3a}$ and $R^{4a}$ have the same meaning as defined above, and the same groups as those mentioned above are preferred.

Of the amide derivatives (3), particularly preferred are compounds in which $R^1$, $R^2$, $R^{3a}$, and $R^{4a}$ in the general formula (3) are groups respectively selected from the particularly preferred groups respectively mentioned above.

In the amide derivative (4) represented by the general formula (4) of the component (A) useful in the practice of the present invention, $R^1$, $R^2$, and $R^3$ have the same meaning as defined above, and $R^{4b}$ is a hydrogen atom, a linear or branched alkoxyl group having 1 to 12 carbon atoms, or an 2,3-epoxypropyloxy group. Specific examples of $R^1$, $R^2$, and $R^3$ include the same groups as those in the amide derivatives (1). Examples of the linear or branched alkoxyl group having 1 to 12 carbon atoms represented by $R^{4b}$ include the same groups as those in $R^4$, with a hydrogen atom, the same alkoxyl groups as those in $R^4$ and a 2,3-epoxypropyloxy group being preferred.

Of the amide derivatives (4), particularly preferred are compounds in which $R^1$, $R^2$, $R^3$, and $R^{4b}$ in the general formula (4) are groups respectively selected from the particularly preferred groups respectively mentioned above.

The amide derivative (1) of the component (A) useful in the practice of the present invention can be obtained, for example, in accordance with the following preparation process:

[Preparation Process]

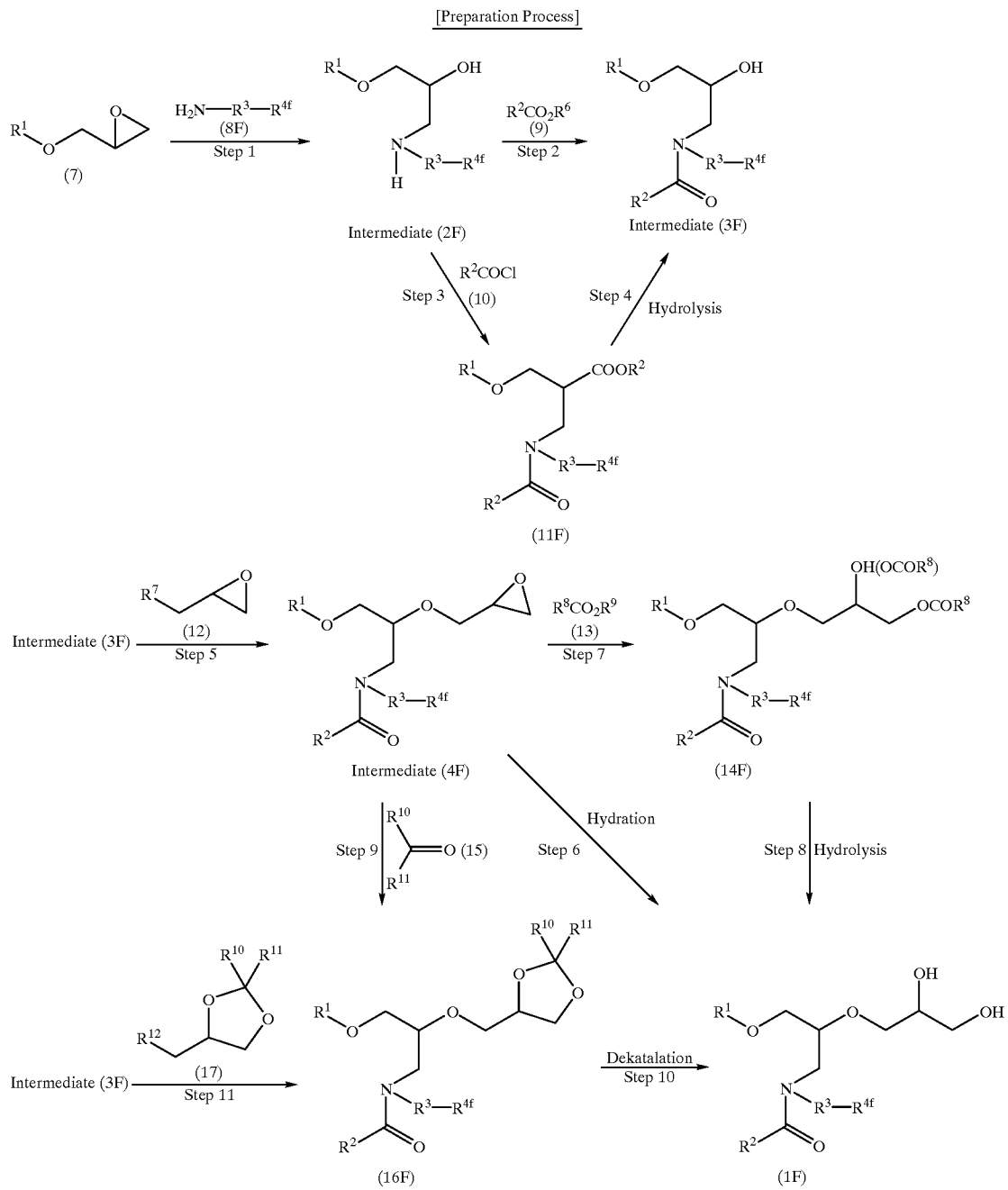

wherein $R^1$, $R^2$, and $R^3$ have the same meaning as defined above, 4f is a hydrogen atom or a linear or branched alkoxyl group having 1 to 12 carbon atoms, with the proviso that when $R^3$ is a single bond, $R^{4f}$ is a hydrogen atom, $R^5$, $R^3$, $R^{10}$, and $R^{11}$ are, independently, a linear or branched and saturated or unsaturated hydrocarbon group having 1 to 8 carbon atoms, preferably, a linear or branched alkyl group having 1 to 5 carbon atoms, particularly preferably, a methyl group, $R^9$ is a hydrogen atom, alkali metal atom or $COR^8$ group, and $R^7$ and $R^{12}$ are leaving groups such as a halogen atom, mesylate group or tosylate group. $R^7$ is preferably a chlorine or bromine atom, particularly, a chlorine atom from the viewpoint of easy availability and the like. $R^{12}$ is a mesylate or tosylate group from the viewpoint of easy availability and the like.

The reaction conditions for the respective steps in the above preparation process are as follows.

Step 1):
Glycidyl ether (7) is reacted with an amine (8F) at a temperature from room temperature to 150° C. either without any solvent or in a solvent, such as water, a lower alcohol such as methanol, ethanol or isopropanol, an ether such as tetrahydrofuran, dioxane or ethylene glycol dimethyl ether, a hydrocarbon such as hexane, benzene, toluene or xylene, or an optionally mixed solvent thereof, whereby an aminoalcohol derivative (2F) can be prepared.

Step 2):
A fatty acid ester (9), preferably, a lower alkyl ester of a fatty acid such as the methyl ester or ethyl ester of a fatty acid is reacted with the aminoalcohol derivative (2F) in the presence of a basic catalyst, such as an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, or an alkali metal alcoholate such as sodium methoxide, sodium ethoxide or potassium tert-butoxide at a temperature from room temperature to 150° C. under a pressure ranging from atmospheric pressure to a reduced pressure of 0.01 mmHg, whereby an amide derivative (3F) can be prepared. At this time, the amount of the basic catalyst to be used is preferably 0.01–0.2 equivalents of the aminoalcohol derivative (2F) In addition, the reaction may preferably be conducted while removing an alcohol formed by the reaction from the system so that the reaction progresses quickly.

Step 3):
The amide derivative (3F) can also be prepared by reacting the aminoalcohol derivative (2F) with a fatty acid chloride (10) at a temperature from room temperature to 100° C. in the presence or absence of a base such as pyridine or a tertiary amine such as triethylamine either without any solvent or in a solvent, such as a halogenated hydrocarbon such as chloroform, methylene chloride or 1,2-dichloroethane, an ether such as tetrahydrofuran, dioxane or ethylene glycol dimethyl ether, a hydrocarbon such as hexane, benzene, toluene or xylene, or an optionally mixed solvent thereof, thereby converting the aminoalcohol derivative into an amide-ester derivative (11F), and then Step 4):
selectively hydrolyzing the ester group of the amide-ester derivative (11F) under basic conditions, i.e., in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, or an alkali metal alcoholate such as sodium methoxide, sodium ethoxide or potassium tert-butoxide.

Step 5):
The amide derivative (3F) is reacted with 1 to 20 equivalents of an epoxide, preferably, epichlorohydrin at room temperature in the presence of 1 to 10 equivalents of an alkali metal hydroxide such as potassium hydroxide or sodium hydroxide, an alkali metal carbonate such as potassium carbonate, an alkaline earth metal hydroxide such as calcium hydroxide, or an alkaline earth metal carbonate such as calcium carbonate without any solvent or in a solvent, such as water, an ether such as tetrahydrofuran, dioxane or ethylene glycol dimethyl ether, a hydrocarbon such as hexane, benzene, toluene or xylene, or an optionally mixed solvent thereof, whereby an amide derivative (4F) can be prepared. At this time, it is preferable from the viewpoint of yield to conduct the reaction in the presence of a phase transfer catalyst, such as a quaternary ammonium salt such as tetrabutylammonium bromide, tetrabutylammonium chloride, hexadecyltrimethylammonium chloride, hexadecyltrimethylammonium bromide, stearyltrimethylammonium chloride or bistetraoxyethylenestearylmethylammonium chloride, or a betaine such as lauryldimethylcarboxyammonium betaine.

Step 6):
The amide derivative (4F) is hydrated at a temperature from room temperature to 300° C. under basic conditions, i.e., in the presence of an alkali metal hydroxide such as potassium hydroxide or sodium hydroxide, an alkaline earth metal hydroxide such as calcium hydroxide, an alkali metal carbonate such as potassium carbonate, or an alkaline earth metal carbonate such as calcium carbonate, under acidic conditions, i.e., in the presence of a mineral acid such as sulfuric acid or hydrochloric acid, a Lewis acid such as boron trifluoride or tin tetrachloride, a carboxylic acid such as acetic acid, tetradecanoic acid or hexadecanoic acid, or a sulfonic acid such as p-toluenesulfonic acid, or under base-acid mixing conditions, whereby an amide derivative (1F) can be prepared.

Step 7);
The amide derivative (1F) can also be prepared by reacting the amide derivative (4F) with a carboxylic acid derivative (13), preferably, a lower fatty acid such as acetic acid, an alkali metal salt of a lower fatty acid such as sodium acetate, or a lower fatty acid anhydride such as acetic anhydride, said compounds may be used either singly or in any combination thereof, in the presence or absence of a basic catalyst, such as a tertiary amine such as triethylamine, thereby converting the amide derivative into an ester-amide derivative (14F), and then Step 8):
selectively hydrolyzing the ester group of the esteramide derivative (14F) under basic conditions, i.e., in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, or an alkali metal alcoholate such as sodium methoxide, sodium ethoxide or potassium tert-butoxide.

Step 9):
Further, the amide derivative (1F) can also be prepared by reacting the amide derivative (4F) with a carbonyl compound (15), preferably, a lower aliphatic ketone such as acetone or methyl ethyl ketone in the presence of an acid catalyst, such as a mineral acid such as sulfuric acid, hydrochloric acid or phosphoric acid, a carboxylic acid such as acetic acid, or a Lewis acid such as boron trifluoride or tin tetrachloride, thereby converting the amide derivative into a 1,3-dioxolanamide derivative (16F), and then Step 10) subjecting the 1,3-dioxolan-amide derivative (16F) to deketalation under acidic conditions, i.e., in the presence of a mineral acid such as sulfuric acid, hydrochloric acid or phosphoric acid, a carboxylic acid such as acetic acid, or a sulfonic acid such as p-toluenesulfonic acid.

Step 11):

The 1,3-dioxolan-amide derivative (16F) can also be prepared by reacting the amide derivative (3F) with a glycerol derivative (17) in the presence of a base, such as an alkali metal hydroxide such as potassium hydroxide or sodium hydroxide: an alkaline earth metal hydroxide such as calcium hydroxide, an alkali metal carbonate such as potassium carbonate, an alkaline earth metal carbonate such as calcium carbonate, or an alkali metal hydride such as sodium hydride either without any solvent or in a solvent, such as an aprotic polar solvent such as N,N-dimethylformamide or dimethylsulfoxide, an ether such as tetrahydrofuran, dioxane or ethylene glycol dimethyl ether, a hydrocarbon such as hexane, benzene, toluene or xylene, or an optionally mixed solvent thereof.

The thus-obtained amide derivative (1) of the component (A) useful in the practice of the present invention can be purified by any known method. When the amide derivative is incorporated into a cosmetic composition, it has excellent effects and performance, and offers no problem of safety even if it is a mixture containing intermediates and by-products without conducting any particular purification and has a purity of 70–100%. Any solvates typified by hydrates are also included in the compounds of the component (A) useful in the practice of the present invention.

Examples of the amide derivatives of the component (A) useful in the practice of the present invention, which are represented by the general formula (1) and obtained in accordance with the above preparation process, include the following compounds:

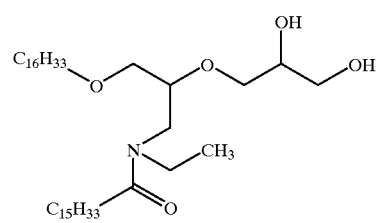

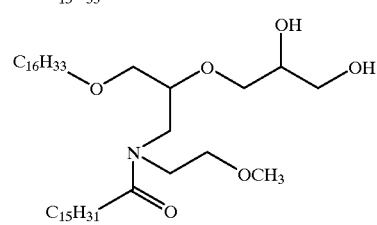

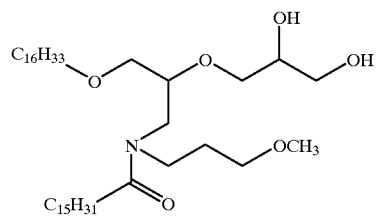

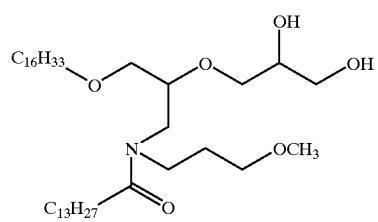

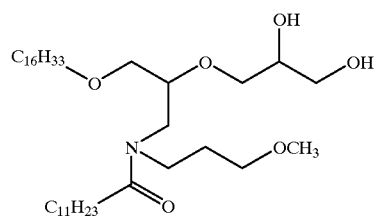

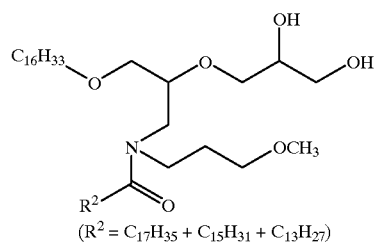

($R^2 = C_{17}H_{35} + C_{15}H_{31} + C_{13}H_{27}$)

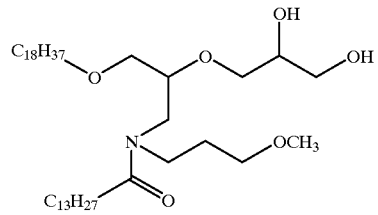

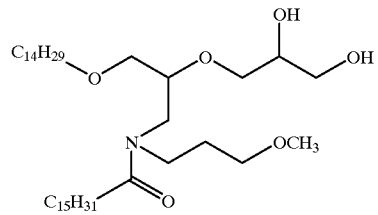

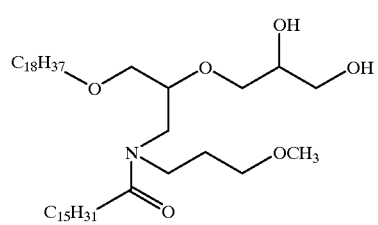

-continued

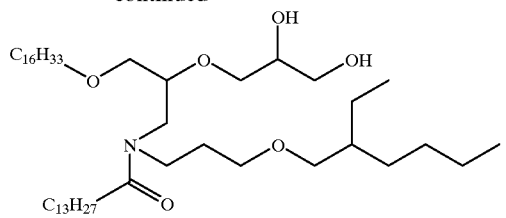

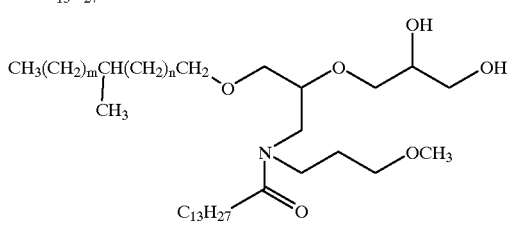

(m and n are such numbers that m+n is 10 to 16, m is 4 to 10, n is 4 to 10, and m and n are distributed with peaks at m=7 and n=7.)

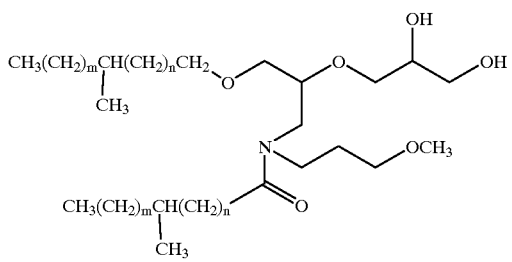

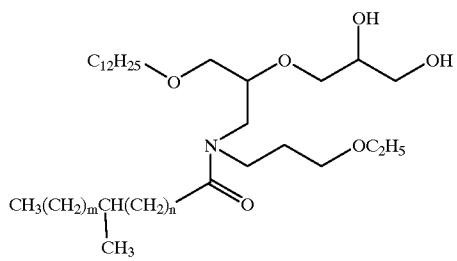

(m and n have the same meaning as defined above)

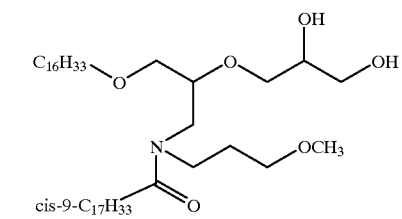

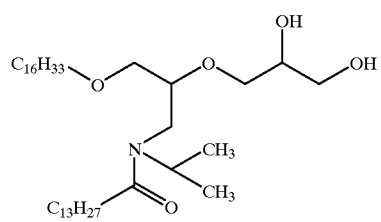

The amide derivatives of the component (A) may be used either singly or in any combination thereof. No particular limitation is imposed on the amount of the component (A) to be incorporated. However, it is particularly preferable from the viewpoint of effects in enhancing the water-retaining ability of the horny layer, improving skin roughness and preventing the formation of wrinkles to incorporate the component (A) in a proportion of 0.001 to 50 wt. % (hereinafter indicated merely by "%"), more preferably 0.1 to 20%, most preferably 0.1 to 10%, based on the total weight of the composition.

No particular limitation is imposed on the polyhydric alcohols of the component (B-1) useful in the practice of the present invention. However, examples thereof include glycerol, polyglycerols such as diglycerol, triglycerol and tetraglycerol, ethylene glycol, 1,3-butylene glycol, 1,4-butylene glycol, propylene glycol, dipropylene glycol, polyethylene glycol, 1,3-propanediol, glucose, mantose, maltitol, sucrose, fructose, xylitol, sorbitol, maltotriose, threitol, erythritol, alcohols obtained by reduction of amylolytic sugar, sorbit, and polyoxyalkylene alkylglucosides. Of these, glycerol, 1,3-butylene glycol, and 1,3-propanediol are particularly preferred.

The polyhydric alcohols of the component (B-1) may be used either singly or in any combination thereof. No particular limitation is imposed on the amount of the component (B-1) to be incorporated. However, it is preferable from the viewpoint of synergistically enhancing the water-retaining ability of the horny layer and enhancing the effects of improving skin roughness and preventing the formation of wrinkles to incorporate the component (B-1) in a proportion of 0.001 to 50%, more preferably 0.01 to 30%, most preferably 0.1 to 20%, based on the total weight of the composition.

Examples of the vegetable extracts of the component (B-2) useful in the practice of the present invention include those obtained from plants such as *Angelica keiskei*, adzuki bean, avocado, hydrangea, *Gynostemma pentaphyllum*, ARUTEKA, arnica, almond, aloe, apricot, nettle, iris, fennel, turmeric, EIJITSU, Scutellariae radix, Amur cork tree, goldthread, barley, gumbo, Saint-John's-wort, dead nettle, ONONISU, watercress, persimmon, the root of kudzu, *Valeriana fauriei*, birch, cattail, chamomile, chamomilla, oats, licorice, raspberry, kiwi, cucumber, apricot, coconut, Cape jasmine, *Sasa albo-marginata*, a walnut, cinnamon, mulberry, GUNJO, gentian, cranesbill, burdock, sesame, wheat, rice, *Camellia sasangua*, saffron, hawthorn, Japanese pepper tree, mushroom, *Rehmannia clutinosa*, prop root, beefsteak plant, Japanese linden, *Filipendula multijuga*, peony, ginger, calamus, white birch, Japanese honeysuckle, field horsetail, *Stevia rebaudiana Bertoni*, western ivy, western hawthorn, elder, needle juniper, milfoil, mint, sage, common mallow, *Cnidium officinale*, Japanese green gentian, soybean, DAISO, thyme, tea plant, clove, dried orange peal, evening primrose, camellia, *Centella asiatica*, English walnut, *Angelica acutiloba*, pot marigold, ginseng, orange peal, corn, *Houttuynia cordata*, tomato, carrot, garlic, wild rose, malt, parsley, rye, adlay, Japanese mint, papaya, hamamelis, rose, white cedar, sunflower, loquat, butterbur, dandelion, grape, placenta, hazelnut, dishcloth gourd, safflower, bo tree, peony, hop, macadamia nut, pine, horse chestnut, melissa, melilot, peach, malt, Rodger's bronze leaf, palm, eucalyptus, creeping saxifrage, lily, YOKUININ, mugwort, rye, peanut, lavender, apple, litchi, lettuce, lemon, Chinese milk vetch, rosemary, camomile, agrimony, Japanese catalpa, hiba arborvitae, HORUTOSO, *Isodon japonicus Hara*, KIJITSU, SENKISHI, chickweed, duckweed, mugwort, ginkgo, Chinese bellflower, chrysanthemum, soapberry and weeping golden bell. Of these, extracts from hamamelis, peony, agrimony, Japanese catalpa, hiba arborvitae, HORUTOSO, *Isodon laponicus Hara* and KIJITSU are particularly preferred in the present invention.

The extracts can be obtained by grinding the whole of the respective plants or one or more of their parts (hereinafter referred to as "stocks" such as leaves, bark, roots, branches, seeds or fruits or nuts, and flowers or blossoms after drying them or without drying them, and then extracting them either with a solvent or by means of an extractor such as a Soxhlet's extractor at ordinary temperature or an elevated temperature. No particular limitation is imposed on the solvent used here. However, examples thereof include known solvents, such as water, primary alcohols such as methyl alcohol and ethyl alcohol, liquid polyhydric alcohols such as propylene glycol and 1,3-butylene glycol, lower alkyl esters such as ethyl acetate, hydrocarbons such as benzene and hexane, ethyl ether, and acetone. These solvents may be used either singly or in any combination thereof. As a preferable specific example of a method for extracting from the stocks, 1,000 ml of 50 v/v % aqueous ethanol are added to 100 grams of a dry ground product to conduct extraction for 3 days while sometimes stirring at room temperature. The resultant extract is filtered, and the filtrate is left at rest for 3 days at 5° C. and then filtered again, thereby obtaining a supernatant. Although the vegetable extract obtained under the above conditions may be used in the form of a solution as extracted, it may be used after treating it by concentration, filtration, drying and/or the like as needed.

The vegetable extracts of the component (B-2) may be used either singly or in any combination thereof. No particular limitation is imposed on the amount of the component (B-2) to be incorporated. However, it is preferable from the viewpoint of achieving sufficient effects in improving skin roughness, preventing the formation of wrinkles and smoothing the wrinkles to incorporate the component (B-2) in a proportion of 0.0001 to 20%, more preferably 0.0001 to 10%, most preferably 0.0001 to 5% in terms of dry solids, based on the total weight of the composition.

No particular limitation is imposed on the organic acids or salts thereof of the component (B-3) useful in the practice of the present invention. However, examples of the organic acids include hydroxycarboxylic acids having 2 to 28 carbon atoms, such as glycolic acid, lactic acid, citric acid and 2-hydroxyoctanoic acid; dicarboxylic acids having 2 to 12 carbon atoms, such as succinic acid, fumaric acid, maleic acid, malonic acid and 1,3-propanedicarboxylic acid; monocarboxylic acids having 10 to 24 carbon atoms, such as stearic acid, palmitic acid, myristic acid, isostearic acid, linolic acid, linolenic acid and arachidonic acid; amino acids such as aspartic acid, asparagin, glycine, glutamic acid, glutamine, γ-aminobutyric acid, arginine, cysteine and alanine; dicarboxylic acid monoesters such as octyl succinate and methyl maleate; and sterol derivatives represented by the general formula (5):

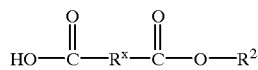

(5)

wherein $R^x$ is —$(CH_2)_l$— (l is a number of 2 to 10),

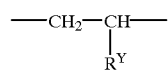

or

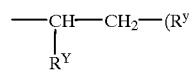

is a linear or branched alkyl or alkenyl group having 6 to 20 carbon atoms), and $R^z$ is a residue of a natural sterol or a hydrogenated product thereof in which a proton of the hydroxyl group is removed.

Of these sterol derivatives, examples of cholesteryl alkenylsuccinates include those synthesized in accordance with the preparation process described in Japanese Patent Application Laid-Open No. 294989/1993, which is incorporated herein by reference, for example, monocholesteryl n-hexadecenylsuccinate and monocholesteryl n-octadecenylsuccinate.

Preferred as the sterol derivative are those of the general formula (5) in which l is 2 to 5, $R^Y$ is hexadecenyl or octadecenyl, and $R^Z$ is cholesteryl or sitosteryl. As the organic acids of the component (B-3), glycolic acid, lactic acid, citric acid, succinic acid and the sterol derivatives are particularly preferred.

No particular limitation is imposed on the salts of the organic acids of the component (B-3). However, examples thereof include salts of lactic acid, citric acid and succinic acid, and acid-addition salts such as, for example, hydrochlorides, sulfates, nitrates and phosphates when an organic acid has a basic group.

The organic acids or the salts thereof of the component (B-3) may be used either singly or in any combination thereof. No particular limitation is imposed on the amount of the component (B-3) to be incorporated. However, it is particularly preferable from the viewpoint of the effects of enhancing the water-retaining ability of the horny layer, improving skin roughness and preventing the formation of wrinkles to incorporate the component (B-3) in a proportion of 0.00001 to 30%, more preferably 0.001 to 20%, based on the total weight of the composition.

In the present invention, the components (B-1), (B-2), and (B-3) may be used either singly or in any combination thereof. The combination of the component (B-i) with the component (B-3) is preferred.

When at least one component selected from the following components (C), (D), (E), (F), (G), and (H) is incorporated into the composition according to the present invention in addition to the above-described essential components, it is possible to further enhance the effects of the present invention.

When an acid hetero-polysaccharide derived from the callus of a plant belonging to Polyanthes L. is incorporated as the component (C), the protective effect of the resulting composition on the skin is increased, so that further enhanced effects in improving skin roughness, preventing the formation of wrinkles and smoothing wrinkles are achieved. It is hence preferable to incorporate such a component.

The acid hetero-polysaccharide (hereinafter referred to as "acid polysaccharide") of the component (C) derived from the callus of a plant belonging to Polyanthes L. can be collected from a culture obtained by culturing the callus derived from a plant belonging to Polyanthes L. Tuberose (*Polyanthes tuberosa L.*) may be mentioned as a preferable example of the plant belonging to Polyanthes L. As the component (C), a modified hetero-polysaccharide derived from the callus of tuberose is preferably used.

In the case of tuberose, the collection of the acid polysaccharide can be conducted, for example, in accordance with the following tissue culture process. Namely, a part of tuberose, such as blossoms, is used as an explant, and $10^{-5}$ M auxin and $10^{-4}$ M cytokinin are added as plant hormones to a Linsmaier-skoog basal medium. Further, 3% saccharose is added as a carbon source. After the thus-prepared medium is used to derive callus, subculture is conducted, and a liquid medium composed of the same components as those used in the callus-culture medium is used to conduct shaking culture. Thereafter, cells are removed from the culture solution by centrifugation, filtration or the like, and the remaining culture solution is concentrated by means of a rotary evaporator or the like. The resultant concentrate is added with a solvent such as ethanol or acetone to precipitate the product. The precipitate is lyophilized, whereby the acid polysaccharide can be separated and collected.

It is preferable from the viewpoint of achieving the more satisfactory effects in preventing the dermal aging to incorporate the thus-obtained acid polysaccharide in a proportion of 0.0001 to 20%, more preferably 0.001 to 10%, most preferably 0.01 to 10, based on the total weight of the composition.

When a sterol is incorporated as the component (D), the penetration of the components (A) and (B) into the skin is facilitated, so that further enhanced effects in improving skin roughness, preventing the formation of wrinkles and smoothing wrinkles are achieved. It is hence preferable to incorporate such a component. Examples of such a sterol include cholesterol and cholesterol derivatives. As examples of the cholesterol derivatives, may be mentioned cholestanol, cholesteryl esters having a saturated or unsaturated and linear or branched hydrocarbon group having 12 to 36 carbon atoms, preferably 14 to 28 carbon atoms, and dehydrocholesterols. Further, examples of the cholesteryl esters include cholesteryl isostearate, cholesteryl 1,2-hydroxystearate, cholesteryl lanolin fatty acid and cholesteryl ricinoleate. Specific examples of the sterols include cholesterol, cholesteryl isostearate, provitamin $D_3$, campesterol, stegmastanol, stegmasterol, 5-dihydrocholesterol, α-spinasterol, palysterol, clionasterol, γ-sitosterol, stegmastenol, sargasterol, apenasterol, ergostanol, sitosterol, colubisterol, chondrillasterol, polyphellasterol, haliclonasterol, neospongosterol, fucosterol, aptostanol, ergostadienol, ergosterol, 22-dihydroergosterol, brassicasterol, 24-methylenecholesterol, 5-dihydroergosterol, dehydroergosterol, fungisterol, cholestanol, coprostanol, zymosterol, 7-hetocholesterol, lathosterol, 22-dehydrocholesterol, β-sitosterol, cholestatrien-3β-ol, coprosterol, cholestenol, ergostenol, 7-dehydrocholesterol, 24-dehydrocholestadien-3β-ol, equilenine, equilin, estrone, 17β-estradiol, androst-4-ene-3β,17β-diol, and dehydroepiandrosterone. These sterols may be used either singly or in any combination thereof.

Of these, cholesterol, cholesteryl isostearate, and cholestanol are particularly preferred.

The sterols of the component (D) may be used either singly or in any combination thereof, and no particular limitation is imposed on its amount to be incorporated. However, it is preferable to incorporate the component (D) in a proportion of 0.01 to 50%, more preferably 0.01 to 40%, most preferably 0.01 to 20%, based on the total weight of the composition.

When an antiphlogistic substance is incorporated as the component (E), the effect of preventing inflammation caused by ultraviolet rays or the like is enhanced, so that further enhanced effects in improving skin roughness, preventing the formation of wrinkles and smoothing wrinkles are achieved. It is hence preferable to incorporate such a component. Examples of such an antiphlogistic substance include glycyrrhizic acid and salts thereof, glycyrrhetinic acid and salts thereof, ε-aminocaproic acid and salts thereof, allantoin, lysozyme hydrochloride, guaiazulene, methyl salicylate, γ-oryzanol and bisabolol. Of these, glycyrrhetinic acid, stearyl glycyrrhetinate, and ε-aminocaproic acid are preferred.

The antiphlogistic substances of the component (E) may be used either singly or in any combination thereof. It is preferable to incorporate the component (E) in a proportion of 0.001 to 5%, more preferably 0.01 to 2%, most preferably 0.01 to 1%, based on the total weight of the composition.

When a singlet oxygen scavenger or antioxidant is incorporated as the component (F), the effect of detoxicating peroxides and active oxygen is enhanced, so that further enhanced effects in improving skin roughness, preventing the formation of wrinkles and smoothing wrinkles are achieved. It is hence preferable to incorporate such a component. Examples of such a singlet oxygen scavenger or antioxidant include carotenoides such as α-carotene, β-carotene, γ-carotene, lycopene, cryptoxanthin, lutein, zeaxanthin, isozeaxanthin, rhodoxanthin, capsanthin, and crocetin; 1,4-diazacyclooctane, 2,5-dimethylfuran, 2-methylfuran, 2,5-diphenylfuran, 1,3-diphenylisobenzofuran, α-tocopherol, β-tocopherol, γ-tocopherol, d-tocopherol, histidine, tryptophan, methionine, and alanine or alkyl esters thereof; tannins such as dibutylhydroxytoluene, butylhydroxyanisole, ascorbic acid, tannic acid, epicatechin, epicarocatechin, epicatechin gallate, and epicarocatechin gallate; flavonoids such as rutin; enzymes such as superoxide dismutases, catalases, glutathione peroxidases, and glutathione reductases; and Ennds, peralchin, platonin, and capsaichin.

Of these, carotenes, tocopherols, ascorbic acid, tannic acid, epicatechin gallate, and epicarocatechin gallate are preferred.

The singlet oxygen scavengers or antioxidants of the component (F) may be used either singly or in any combination thereof. It is preferable to incorporate the component (F) in a proportion of 0.001 to 5%, more preferably 0.01 to 2%, most preferably 0.01 to 1% based on the total weight of the composition.

The cosmetic compositions according to the present invention include both skin cosmetic compositions and hair cosmetic compositions.

When an amine derivative represented by the general formula (b):

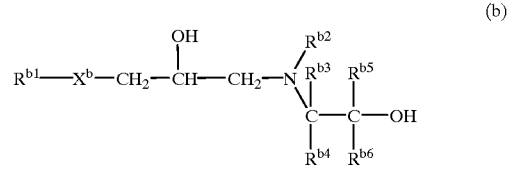

(b)

wherein $R^{b1}$ is a linear, branched or cyclic hydrocarbon group having 1 to 40 carbon atoms, which may be substituted by at least one hydroxyl group, or a hydrocarbon group having 1 to 5 carbon atom and containing a heteroatom, $R^{b2}$, $R^{b3}$, $R^{b4}$, and $R^{b5}$ are identical to or different from one another and are, independently, a hydrogen atom or a hydrocarbon group having 1 to 20 carbon atoms, which may be substituted by at least one hydroxyl group, and Xb is —O— or —CO—O— with the proviso that the carbonyl group is bonded to $R_{b1}$, or an acid addition salt thereof is incorporated as the component (G), the effects of improving skin roughness, preventing the formation of wrinkles and smoothing wrinkles, which are brought about by the amine derivative or the acid-addition salt thereof, act synergistically, so that further enhanced effects in improving skin roughness, preventing the formation of wrinkles and smoothing wrinkles are achieved. It is hence preferable to incorporate such a component. Such an amine derivative is that represented by the general formula (b). Examples of the linear, branched or cyclic hydrocarbon group having 1 to 40 carbon atoms represented by $R^{b1}$ in the general formula (b) include alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontyl, hexatriacontyl, heptatriacontyl, octatriacontyl, nonatriacontyl, tetracontyl, methyl-branched isostearyl, 2-ethylhexyl, 2-heptylundecyl, 5,7,7-trimethyl-2-(1,3,3-trimethylbutyl)octyl, and isopropyl groups; alkenyl groups such as vinyl, allyl, butenyl, pentenyl, hexenyl, 9-octadecenyl, and 9,12-octadecadienyl groups; alicyclic hydrocarbon groups such as cyclopropyl, cyclobutyl, cyclopentyl, and cyclohexyl groups; aromatic hydrocarbon groups such as phenyl, naphthyl, tolyl, xylyl, and benzyl groups; and hydrocarbon groups such as a cholesteryl group.

These hydrocarbon groups may be substituted by one or more hydroxyl groups. Examples of such groups include hydroxymethyl, hydroxyethyl, hydroxypropyl, hydroxyhexyl, 2,3-dihydroxypropyl, and 2,2-bis(hydroxymethyl)-3-hydroxypropyl groups.

In the hydrocarbon group having 1 to 5 carbon atoms containing a heteroatom represented by $R^{b1}$, examples of the heteroatom include oxygen, nitrogen, sulfur, phosphorus, and fluorine atoms. Examples of the hydrocarbon groups containing these atoms include glycosyl, carboxymethyl, aminocarbonylmethyl, and 1-(N,N-dimethylamino)ethyl groups.

Examples of the hydrocarbon groups having 1 to 20 carbon atoms represented by $R^{b2}$, $R^{b3}$, $R^{b4}$, $R^{b5}$, and $R^{b6}$ include hydrocarbon groups, such as alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methyl-branched isostearyl, 2-ethylhexyl, 2-heptylundecyl, 5,7,7-trimethyl-2-(1,3,3-trimethylbutyl) octyl, and isopropyl groups; alkenyl groups such as vinyl, allyl, butenyl, pentenyl, hexenyl, 9-octadecenyl, and 9,12-octadecadienyl groups; alicyclic hydrocarbon groups such as cyclopropyl, cyclobutyl, cyclopentyl, and cyclohexyl groups; and aromatic hydrocarbon groups such as phenyl, naphthyl, tolyl, xylyl, and benzyl groups.

These hydrocarbon groups may be substituted by one or more hydroxyl groups. Examples of such groups include hydroxymethyl, 2-hydroxyethyl, 2-hydroxypropyl, 1,2-dihydroxyethyl, 1,2,3-trihydroxypropyl, 1,2,3-trihydroxybutyl, 1,2,3,4-tetrahydroxybutyl, 1,2,3,4-tetrahydroxypentyl, and 1,2,3,4,5-pentahydroxypentyl groups. of such amine derivatives (b), those in which X is —O—, and $R^{b2}$, $R^{b3}$, $R^{b4}$, $R^{b5}$, and $R^{b6}$ are hydrogen atoms are known compounds (Japanese Patent Application Laid-open No. 228048/1987, which is incorporated herein by reference). However, their effects on the skin have not been known at all.

The amine derivatives (b) useful in the practice of the present invention are synthesized in accordance with various known processes. For example, they may be synthesized by reacting glycidyl ether or an ester derivative thereof (c) with an amine derivative (d) in accordance with the following reaction scheme:

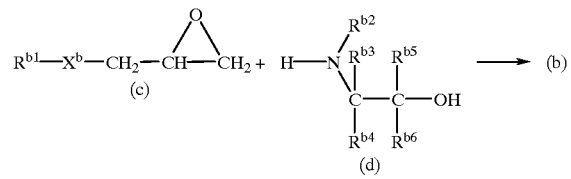

wherein $R^{b1}$, $R^{b2}$, $R^{b3}$, $R^{b4}$, $R^{b5}$, and $R^{b6}$ have the same meaning as defined above.

The amine derivative (b) thus obtained may be converted into an inorganic acid salt with hydrochloric acid, sulfuric acid, nitric acid or phosphoric acid, or an organic acid salt with succinic acid, fumaric acid, hexadecanoic acid, octadecanoic acid, lactic acid, glycolic acid, citric acid, tartaric acid or benzoic acid in accordance with the methods known per se in the art as needed.

Particularly preferred as the amine derivatives of the component (G) are 1-(2-hydroxyethylamino)-3-isostearyloxy-2-propanol, 1-(2-hydroxyethylamino)-3-(12-hydroxystearyloxy)-2-propanol, and 1-(2-hydroxyethylamino)-3-methyloxy-2-propanol.

The amine derivatives and acid-addition salts thereof of the component (G) may be used either singly or in any combination thereof. No particular limitation is imposed on the amount of the component (G) to be incorporated. However, it is preferable to incorporate the component (G) in a proportion of 0.0001 to 10%, more preferably 0.0001 to 2%, most preferably 0.001 to 1%, based on the total weight of the composition.

When a guanidine derivative represented by the general formula (e) or (f):

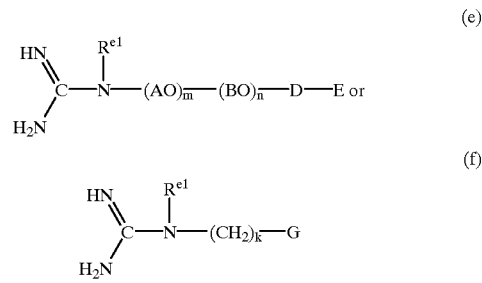

wherein in the formula (e), A and B may be identical to or different from each other and are, independently, an alkylene group having 2 to 8 carbon atoms, D is a bond, —CO— or an alkylene group having 1 to 6 carbon atoms, which may have a substituent, E is a hydrogen atom, lower alkyl group, aralkyl group or an aryl group which may have a substituent, m is a number of 1 to 6, n is a number of 0 to 6, $R^{e1}$ is a hydrogen atom, lower alkyl group or —$(AO)_m$—$(BO)_n$—D—E, with the proviso that when $R^{e1}$ is a methyl group, —$(AO)_m$—$(BO)_n$—D—E is not a hydroxyethyl group, and in the formula (f), k is a number of 1 to 10, G is a hydrogen atom, hydroxyl group, carboxyl group, sulfonic group or phosphoric group, and $R^{e1}$ has the same meaning as defined above, or an acid-addition salt thereof is incorporated as the component (H), the effects of improving skin roughness, preventing the formation of wrinkles and smoothing wrinkles, which are brought about by the guanidine derivative or the acid-addition salt thereof, act synergistically, so that further enhanced effects in improving skin roughness, preventing the formation of wrinkles and smoothing wrinkles are achieved. It is hence preferable to incorporate such a component. Such an guanidine derivative is that represented by the general formula (e) or (f). The alkylene groups having 2 to 8 carbon atoms represented by A and B in the general formula (e) may be either linear or branched, and examples thereof include ethylene, trimethylene, tetramethylene, pentamethylene, hexamethylene, and propylene groups. Of these, those having 2 to 6 carbon atoms are preferred with those having 2 to 4 carbon atoms being particularly preferred. Preferable specific examples thereof include ethylene, trimethylene, and propylene groups.

The alkylene group having 1 to 6 carbon atoms represented by D may be either linear or branched, and examples thereof include methylene, ethylene, trimethylene, tetramethylene, pentamethylene, hexamethylene, and propylene groups.

Examples of the lower alkyl group represented by E or $R^{e1}$ include linear or branched alkyl groups having 1 to 5 carbon atoms. Specific examples thereof include methyl, ethyl, n-propyl, isopropyl, n-butyl, sec-butyl, tert-butyl, and pentyl groups. Of these a methyl group is particularly preferred.

Examples of the aralkyl group represented by E include those having 7 to 12 carbon atoms, such as benzyl, phenethyl, and naphthylmethyl groups.

Examples of the aryl group represented by E include phenyl and naphthyl groups. Examples of the substituent thereof include an amino group which may be substituted by a lower alkyl group such as a methyl group; a nitro group; a cyano group; a hydroxyl group; a carboxylic residue which may be in an ester form with a lower alkyl group, halogenated lower alkyl group or aralkyl group; a carbamoyl group; halogen atoms such as fluorine, chlorine, bromine and iodine; lower alkyl groups such as methyl, ethyl, propyl and isopropyl groups; and lower alkoxyl groups such as methoxy and ethoxy groups.

m is a number of 1 to 6, preferably 1 to 4. n is a number of 0 to 6, preferably 0 to 4.

In the general formula (f), $R^{e1}$ has the same meaning as defined above. k is a number of 1 to 10, preferably 1 to 5. G is preferably a hydroxyl, carboxyl or phosphoric group.

Examples of the guanidine derivatives representedby such a general formula (e) or (f) include 2-hydroxyethylguanidine, 3-hydroxypropylguanidine, 2-hydroxypropylguanidine, 4-hydroxybutylguanidine, 5-hydroxypentylguanidine, 6-hydroxyhexylguanidine, 2-(2-hydroxyethoxy)ethylguanidine, 2-[2-(2-hydroxyethoxy)ethoxy]ethylguanidine, 1-(3-hydroxypropyl)-1-methylguanidine, 1-(2-hydroxypropyl)-1-methylguanidine, 1-(4-hydroxybutyl)-1-methylguanidine, 1-(5-hydroxypentyl)-1-methylguanidine, 1-(6-hydroxyhexyl)-1-methylguanidine, 1-[2-(2-hydroxyethoxy)ethyl]-1-methylguanidine, 1-[2-(2-(2-hydroxyethoxy)ethoxy)ethyl3-1-methylguanidine, 1,1-bis(2-hydroxyethyl)guanidine, 1,1-bis(3-hydroxypropyl)guanidine, 1,1-bis(2-hydroxypropyl)guanidine, 1,1-bis(4-hydroxybutyl)guanidine, 1,1-bis(5-hydroxypentyl)guanidine, 1,1-bis(6-hydroxyhexyl)guanidine, 1,1-bis [2-(2-hydroxyethoxy)ethyl]guanidine, 1,1-bis[2-(2-(2-hydroxyethoxy)ethoxy)ethyl]guanidine, (2-methoxyethyl)guanidine, (2-meethoxyethylm)guanidine, (2-ethoxyethyl)guanidine, (3-methoxypropyl)guanidine, (2-methoxypropyl)guanidine, (4-methoxybutyl)guanidine, (5-methoxypentyl)guanidine, 2-(2-methoxyethoxy) ethylguanidine, [2-(2-(2-methoxyethoxy)ethoxy)ethyl] guanidine, 1,1-bis(2-methoxyethyl)guanidine, 1,1-bis(2-ethoxyethyl)guanidine, 1,1-bis(3-methoxypropyl)guanidine, 1,1-bis(2-methoxypropyl)guanidine, 1,1-bis(4-methoxybutyl)guanidine, 1,1-bis(5-methoxypentyl) guanidine, 1,1-bis(6-methoxyhexyl)guanidine, 1,1-bis[2-(2-methoxyethoxy)ethyl]guanidine, 1,1-bis[2-(2-(2-methoxyethoxy)ethoxy)ethyl]guanidine, 1-(2-methoxyethyl)-1-methylguanidine, 1-(2-ethoxyethyl)-1-methylguanidine, 1-(3-methoxypropyl)-1-methylguanidine, 1-(2-methoxypropyl)-1-methylguanidine, 1-(4-methoxybutyl)-1-methylguanidine, 1-(5-methoxypentyl)-1-methylguanidine, 1-(6-methoxyhexyl)-1-methylguanidine, 1-[2-(2-methoxyethoxy)ethyl-1-methyl]guanidine, 1-[2-(2-(2-methoxyethoxy)ethoxy)ethyl]-1-methylguanidine, 2-guanidinoethyl acetate, 3-guanidinopropyl acetate, 2-guanidino-2-propyl acetate, 4-guanidino-1-butyl acetate, 5-guanidino-1-pentyl acetate, 6-guanidino-1-hexyl acetate, 2-(2-guanidinoethoxy)ethyl acetate, 2-[2-(2-guanidinoethoxy)ethoxy]ethyl acetate, 2-(1-methylguanidino)ethyl acetate, 3-(1-methylguanidino) propyl acetate, 2-(1-methylguanidino)-1-methylethyl acetate, 4-(1-methylguanidino)butyl acetate, 5-(1-methylguanidino)pentyl acetate, 6-(1-methylguanidino) hexyl acetate, 2-[2-(1-methylguanidino)ethoxy]ethyl acetate, 2-[2-(2-(1-methylguanidino)ethoxy)ethoxy]ethyl acetate, 2-guanidinoethyl benzoate, 3-guanidinopropyl benzoate, 2-guanidino-2-propyl benzoate, 4-guanidino-1-butyl benzoate, 5-guanidinol-1-pentyl benzoate, 6-guanidino-1-hexyl benzoate, 2-(2-guanidinoethoxy)ethyl benzoate, 2-[2-(2-guanidinoethoxy)ethoxy]ethyl benzoate, 2-(1-methylguanidino)ethyl benzoate, 3-(1-methylguanidino)propyl benzoate, 2-(1-methylguanidino)-1-methylethyl benzoate, 4-(1-methyl-guanidino)butyl benzoate, 5-(1-methylguanidino)pentyl benzoate, 6-(1-methylguanidino)hexyl benzoate, 2-[2-(1-methylguanidino) ethoxy]ethyl benzoate, 2-[-2-(2-(1-methylguanidino) ethoxy)ethoxy]ethyl benzoate, 2-guanidinoethyl salicylate, 3-guanidinopropyl salicylate, 2-guanidino-2-propyl salicylate, 4-guanidino-1-butyl salicylate, 5-guanidino-1-pedntyl salicylate, 6-guanidino-1-hexyl salicylate, 2-(2-guanidinoethoxy)ethyl salicylate, 2-[2-(2-guanidinoethoxy) ethoxy]ethyl salicylate, 2-(1-methylguanidino)ethyl salicylate, 3(1-methylguanidino)propyl salicylate, 2-(1-methylguanidino)1-methylethyl salicylate, 4-(1-methylguanidino)butyl salicylate, 5-(1-methylguanidino) pentyl salicylate, 6-(1-methylguanidino)hexyl salicylate, 2-[2-(1-methylguanidino)ethoxy]ethyl salicylate, 2-[2-(2-(1-methylguanidino)ethoxy)ethoxy]ethyl salicylate, 2-guanidinoethyl n- or p-hydroxybenzoate, 3-guanidinopropyl m- or p-hydroxybenzoate, 2-guanidino-2-propyl m- or p-hydroxybenzoate, 4-guanidino-1-butyl m- or p-hydroxybenzoate, 5-guanidino-1-pentyl m- or p-hydroxybenzoate, 6-guanidino-1-hexyl m- or p-hydroxybenzoate, 2-(2-guanidinoethoxy)ethyl m- or p-hydroxybenzoate, 2[2-(-quanidinoethoxy)ethoxy]ethyl m- or phydroxybenzoate, 2-(1-methylguanidino)ethyl m- or p-hydroxybenzoate, 3-(1-methylguanidino)propyl m- or p-hydroxybenzoate, 2-(1-methylguanidino)-1-methylethyl m- or p-hydroxybenzoate, 4-(1-,methylguanidino)butyl m- or p-hydroxybenzoate, 5-(1-methylguanidino)pentyl m- or p-hydroxybenzoate, 6-(1-methylguanidino)hexyl m- or p-hydroxybenzoate, 2-[2-(1-methylguanidino)ethoxy]ethyl m- or p-hydroxybenzoate, 2-[2-(2-(1-methylguanidino) ethoxy)ethoxy]ethyl m- or p-hydroxybenzoate, 3-guanidinopropionic acid and 2-guanidinoethyl dihydrogenphosphate.

Of these, guanidine derivatives, 2-(2-hydroxyethoxy) ethylguanidine, 5-hydroxypentylguanidine, 3-guanidinopropionic acid, and 2-guanidinoethyl dihydrogenphosphate are particularly preferred.

The acid used in forming an acid-addition salt of the guanidine derivative may be either an organic acid or an inorganic acid. Examples thereof include monocarboxylic acids such as formic acid, acetic acid, propionic acid, butyric acid, isobutyric acid, hexanoic acid, heptanoic acid, octanoic acid, nonanoic acid, decanoic acid, lauric acid, myristic acid, palmitic acid, stearic acid, acrylic acid, methacrylic acid, crotonic acid, isocrotonic acid, phenylacetic acid, cinnamic acid, benzoic acid, sorbic acid, nicotinic acid, urocanic acid, and pyrrolidonecarboxylic acid; dicarboxylic acids such as oxalic acid, malonic acid, succinic acid, glutamic acid, adipic acid, pimelic acid, cork acid, azelaic acid, sebacic acid, maleic acid, fumaric acid, phthalic acid, and terephthalic acid; hydroxy acids such as glycolic acid, lactic acid, malic acid, tartaric acid, citric acid, and o-, m- and p-hydroxybenzoic acids; amino acids such as glycine, alanine, β-alanine, valine, leucine, phenylalanine, tyrosine, serine, threonine, methionine, cysteine, cystine, proline, hydroxyproline, pipecolic acid, tryptophan, aspartic acid, asparagine, glutamic acid, glutamine, lysine, histidine, ornithine, arginine, and aminobenzoic acid; lower alkylsulfonic acids such as methanesulfonic acid and trifluoromethanesulfonic acid; arylsulfonic acid such as benzenesulfonic acid, and p-toluenesulfonic acid; hydrohalogenic acids such as hydrofluoric acid, hydrochloric acid, hydrobromic acid, and hydroiodic acid; and inorganic acids such as perchloric acid, sulfuric acid, nitric acid, phosphoric acid, and carbonic acid.

Of these, the guanidine derivatives represented by the formula (e) and acid-addition salts thereof are novel compounds. They may be prepared by reacting a guanidylating reagent with an amine derivative (g), for example, in accordance with the following reaction scheme:

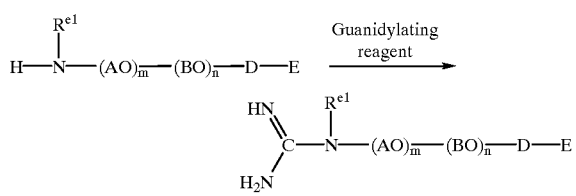

wherein A, B, D, E, m, n and $R^{e1}$ have the same meaning as defined above.

Specific examples of the amine derivative (g), which is a raw material, include 2-(2-aminoethoxy)ethanol, 2-(2(2-aminoethoxy)ethoxy)ethanol, 1-amino-2-propanol, 2-(2-N-methylaminoethoxy)ethanol, 2-(2-(2-N-methylaminoethoxy)ethoxy)ethanol, 1-N-methylamino-2-propanol, N,N-bis-(2-(2-hydroxyethoxy)ethyl)amine, N,N-bis-(2-(2-hydroxyethoxy)ethoxy)ethyl)amine, N,N-di-(2-hydroxypropyl)amine, 3-N-methylamino-1-propanol, 4-N-methylamino-1-butanol, 5-N-methylamino-1-pentanol, 6-N-methylamino-1-hexanol, di-3-propanolamine, di-4-butanolamine, di-5-pentanolamine, di-6-hexanolamine, 2-(2-methoxyethoxy)ethylamine, 2-[2-(2-methoxyethoxy) ethoxy]ethylamine, 2-methoxy-1-propylamine, N-methyl-2-(2-methoxyethoxy)ethylamine, N-methyl-2-[2-(2-methoxyethoxy)ethoxy]ethylamine, N-methyl-2-methoxypropylamine, N,N-bis[2-(2-methoxyethoxy)ethyl] amine, N,N-bis-[2(2-(2-methoxyethoxy)ethoxy)ethyl] amine, N,N,-di-2methoxypropylamine, N-methyl-3-methoxypropylamine, N-methyl-4-methoxybutylamine, N-methyl-5-methoxypentylamine, N-methyl-6-methoxyhexylamine, N,N-di-3-methoxypropylamine, N,N-4-methoxybutylamine, N,N-di-5-methoxypentylamine, and N,N-di-6-methoxyhexylamine.

The quanidine derivatives and acid-addition salts thereof of the component (H) may be used either singly or in any combination thereof. The component (H) is incorporated in a proportion of 0.001 to 50%, preferably 0.001 to 30%, more preferably 0.01 to 20%, based on the total weight of the composition.

The skin cosmetic compositions according to the present invention may further contain surfactants as needed. As such a surfactant, any of nonionic surfactants, anionic surfactants, and amphoteric surfactants may be suitably used.

Examples of the nonionic surfactants include polyoxyethylene alkyl ethers, polyoxyethylene alkyl phenyl ethers, polypxyethylene fatty acid esters, sorbitan fatty acid esters, polyoxyethylene sorbitan fatty acid esters, polyoxyethylene sorbitol fatty acid esters, fatty acid nonoglycerides, polyoxyethylene hardened castor oil, polyoxyethylene hardened castor oil alkylsulfates, polyoxyethylene alkylsulfates, polyglycerol fatty acid esters, sucrose fatty acid esters, glycerol fatty acid esters, alkylphosphates, polyoxyethylene alkyl phosphates, alkali metal salts of fatty acids, and alkyl glyceryl ethers. Among these, glyceryl ethers represented by the following general formula (18):

$$R^{13}\text{—}OCH_2\text{—}\underset{OH}{CH}\text{—}CH_2OH \tag{18}$$

wherein $R^{13}$ is an alkyl group having 8 to 24 carbon atoms, are preferred. Particularly preferred are glyceryl ethers of the formula (18) in which $R^{13}$ is represented by the following formula (19):

$$CH_3\text{—}(CH_2)_{\overline{p}}\text{—}\underset{CH_3}{CH}\text{—}(CH_2)_{\overline{q}}\text{—} \tag{19}$$

wherein p is an integer of 4 to 10, q is an integer of 5 to 11, and p+q is 11 to 17 and is distributed with a peak at q=8.

Examples of the anionic surfactants include linear or branched alkylbenzenesulfonates, linear or branched alkyl (or alkenyl) ether sulfates, alkyl- or alkenylsulfates having an alkyl or alkenyl group, olefinsulfonate, alkanesulfonates, unsaturated fatty acid salts, alkyl (or alkenyl) ether carboxylates, α-sulfo-fatty acid salts or esters having an alkyl or alkenyl group, N-acylamino acid type surfactants having an acyl group and a free carboxylic acid residue, and mono- or diphosphate type surfactants having an alkyl or alkenyl group.

Examples of the amphoteric surfactants include imidazoline type amphoteric surfactants having an alkyl, alkenyl or acyl group, and carbobetaine, amidobetaine, sulfobetaine, hydroxysulfobetaine and amidosulfobetaine type amphoteric surfactants.

These surfactants may be used either singly or in any combination thereof. When these surfactants are incorporated, they may preferably be incorporated in a proportion of 0.01 to 20%, more preferably 0.1 to 5%, based on the total weight of the composition.

The skin cosmetic compositions according to the present invention may further contain oily substances. No particular limitation is imposed on the oily substance, and examples thereof include hydrocarbons such as solid and liquid paraffins, vaseline, crystal oil, ceresin, ozocerite, montan wax, squalane and squalene; ester oils such as eucalyptus oil, hardened palm oil, coconut oil, peppermint oil, evening primrose oil, beeswax, camellia oil, almond oil, cacao oil, castor oil, sesame oil, macadamia nut oil, sunflower oil, peanut oil, avocado oil, beef tallow, lard, horse fat, yolk fat, olive oil, carnauba wax, lanolin, hydrogenated lanolin, jojoba oil, glyceryl monostearate, glyceryl distearate, glyceryl monooleate, myristyl palmitate, cetyl palmitate, cetyl 16-hydroxypalmitate, cetyl isooctanoate, isopropyl palmitate, isobutyl palmitate, isopropyl stearate, butyl stearate, isocetyl stearate, isopropyl myristate, 2-octyldodecyl myristate, hexyl laurate, isopropyl laurate, decyl oleate, neopentylglycol caprate, diethyl phthalate, myristyl lactate, diisopropyl adipate, hexadecyl adipate, cetyl myristate, myristyl lactate, diisostearyl malate, diisopropyl adipate, cetyl lactate, 1-isostearyl-3-myristoylglycerol, cetyl 2-ethylhexanoate, 2-ethylhexyl palmitate, neopentylglycol di-2-ethylhexanoate, 2-octyldodecyl oleate, glycerol triisostearate, glyceryl di-p-methoxycinnamate-mono-2-ethylhexanoate, pentaerythritol tetraesters, glycerol triesters, and glycerol tri-2-ethylhexanoate; higher alcohols such as benzyl alcohol, isocetyl alcohol, isostearyl alcohol, behenyl alcohol, hexadecyl alcohol, phenylethyl alcohol, cetanol, stearyl alcohol, oleyl alcohol, 2-octyldodecanol, palmityl alcohol, and 2-hexyldecanol; and phospholipids, naturally extracted sphingosine derivatives and synthetic substances thereof (for example, glycosyl ceramides, glactosyl ceramides, ceramides, etc.). These oily substances may be used either singly or in any combination thereof.

When these oily substances are incorporated, they may preferably be incorporated in a proportion of 0.001 to 50%, particularly preferably 0.005 to 30% based on the total weight of the composition.

The skin cosmetic compositions according to the present invention may further contain powders. Examples of these powders include inorganic powders such as silicic acid, silicic acid anhydride, magnesium silicate, talc, kaolin, mica, bentonite, mica coated with titanium, iron oxide red, bismuth oxychloride, zirconium oxide, magnesium oxide, zinc oxide, titanium oxide, calcium carbonate, magnesium carbonate, iron oxide, ultramarine blue, iron blue, chromium oxide, chromium hydroxide, calamine, zeolite, and carbon black; various resin powders such as polyamide, polyester, polyethylene, polypropylene, polystyrene, polyurethane, vinyl resins, urea resins, phenol resins, fluororesins, silicone resins, acrylic resins, melamine resins, epoxy resins, polycarbonate resins and divinylbenzene-styrene copolymers, and copolymer resin powers composed of two or more resins thereof; organic powders such as Celluloide, acetylcellulose, polysaccharides, proteins, and scleroproteins; various organic pigment powders such as Red Color No. 201, Red Color No. 202, Red Color No. 204, Red Color No. 205, Red Color No. 220, Red Color No. 226, Red Color No. 228, Red Color No. 405, Orange Color No. 203, orange Color No. 204, Yellow Color No. 204, Yellow Color No. 401, and Blue Color No. 404; pigment powders composed of zirconium, barium or aluminum lake, or the like, such as Red Color No. 3, Red Color No. 104, Red Color No. 106, Red Color No. 227, Red Color No. 230, Red Color No. 401, Red Color No. 505, orange Color No. 205, Yellow Color No. 4, Yellow Color No. 5, Yellow Color No. 202, Yellow Color No. 203, Green Color No. 3 and Blue Color No. 1; and metal soaps such as magnesium stearate., calcium stearate, zinc laurate and zinc palmitate. These powders may be subjected to a surface treatment such as a silicone treatment with methyl hydrogenmethylpolysiloxane, trimethylsiloxysilicic acid, methylpolysiloxane or the like; a fluorine treatment with a perfluoroalkyl phosphate, perfluoroalcohol or the like; an amino acid treatment with N-acylglutamic acid or the like; a lecithin treatment, a metal soap treatment, a fatty acid treatment or an alkylphosphate treatment before their use. Two or more of these powders may also be used in combination.

When these powders are incorporated, their proportion in the skin cosmetic composition may be suitably determined according to the preparation form of the composition. However, it is generally preferable to incorporate them in a proportion of 0.001 to 50%, particularly preferably 0.005 to 30% based on the total weight of the composition.

The skin cosmetic compositions according to the present invention may further contain silicones. No particular limitation is imposed on the silicones so far as they are routinely incorporated in cosmetic compositions. Examples thereof include octamethylpolysiloxane, tetradecamethylpolysiloxane, methylpolysiloxane, high-polymeric methylpolysiloxane and methylphenylpolysiloxane, and besides methylpolycyclosiloxanes such as octamethylcyclotetrasiloxane and decamethylcyclopentasiloxane, trimethylsiloxysilicic acid, and modified silicones such as polyether-alkyl-modified silicones and specific modified organopolysiloxanes described in Japanese Patent Application Laid-Open No. 72851/1994, which is incorporated herein by reference.

When these silicones are incorporated, their proportion in the skin cosmetic composition may be suitably determined according to the preparation form of the composition. However, it is generally preferable to incorporate them in a proportion of 0.001 to 50%, particularly preferably 0.005 to 30% based on the total weight of the composition.

The skin cosmetic compositions according to the present invention nay further contain various polysaccharides. Examples of such polysaccharides include xanthan gum, cationic cellulose, sodium hyaluronate, chitin alginate, chitosan, carboxymethylcellulose, methylhydroxypropylcellulose, ι-carrageenan, λ-carrageenan, pullulan, Jew's-ear, ghatti gum, trehalose, and agar.

When these polysaccharides are incorporated, they may be used either singly or in any combination thereof. It is preferable to incorporate them in a proportion of 0.0001 to 20%, particularly preferably 0.001 to 10%, based on the total weight of the composition.

The skin cosmetic compositions according to the present invention may further contain various amino acids. Examples of such amino acids include neutral amino acids such as glycine, serine, cystine, alanine, threonine, cysteine, valine, phenylalanine, methionine, leucine, tyrosine, proline, isoleucine, tryptophan, and hydroxyproline; acidic amino acids such as aspartic acid, asparagine, glutamine and glutamic acid; basic amino acids such as arginine, histidine and lysine; and besides, as betaine and amino acid derivatives, acylsarcosine and salts thereof, acylglutamic acid and salts thereof, acyl-β-alanine and salts thereof, glutathione, pyrrolidonecarboxylic acid and salts thereof; and oligopeptides such as glutathin, carnosin, gramcidin S, tyrocidine A and tyrocidine B, and guanidine derivatives and salts thereof described in Japanese Patent Application Laid-open No. 228023/1994, which is incorporated herein by reference.

When these amino acids are incorporated, they may be used either singly or in any combination thereof. It is preferable to incorporate them in a proportion of 0.001 to 50%, particularly preferably 0.001 to 30%, based on the total weight of the composition.

The skin cosmetic compositions according to the present invention may further contain film-forming ingredients. Examples of such film-forming ingredients include vinyl polymers such as polyvinyl alcohol, polyvinyl pyrrolidone, sodium polyacrylate; emulsions such as chitosan pullulan emulsions and alkyl acrylate copolymer emulsions; polypeptides such as soluble collagen, hydrolyzed elastin, and silk extract; and polyethylene glycol having a molecular weight of 20,000 to 4,000,000.

When these film-forming ingredients are incorporated, they may preferably be incorporated in a proportion of 0.001 to 1o0, particularly preferably 0.001 to 5% based on the total weight of the composition.

The skin cosmetic compositions according to the present invention may further contain a pH adjustor. No particular limitation is imposed on such pH adjustor. However, examples thereof include metal hydroxides such as sodium hydroxide, potassium hydroxide and lithium hydroxide, triethanolamine, isopropanolamine, diisopropanolamine, urea, ϵ-aminocarponic acid, sodium pyrrolidone carboxylate, sodium hydrogenphosphate, and betaines such as glycine betaine and lysine betaine.

The skin cosmetic compositions according to the present invention are preferably adjusted to a pH within a range of 2 to 11, particularly 3 to 10.

Besides the above ingredients, various ingredients incorporated routinely in cosmetic compositions, quasidrugs, drugs and the like may be incorporated in the skin cosmetic compositions according to the present invention within limits not impeding the object of the present invention. As examples of such ingredients, may be mentioned inorganic salts such as magnesium sulfate, potassium sulfate, sodium sulfate, magnesium chloride and sodium chloride; viscosity modifiers such as polyvinyl alcohol, carboxyvinyl polymers, gelatin, tragacanth gum, pectin, mannan, locust bean gum, galactan, gum arabic, xanthan gum, dextran, succinoglucan, curdlan, quince seed, soageena, casein, albumin, sodium polyacrylate, polyvinyl pyrrolidone, poly (vinyl methyl ether), hydroxyethylcellulose, ethylcellulose, hydroxypropylcellulose, starch, carboxymethyl starch, methyl starch, agarose, propylene glycol alginate, and guar gum; hydrophilic moisture-absorbing substances known as natural moisturizing factors (NMF), or derivatives thereof; antiseptics such as parabens, and dehydroacetic acid and salts thereof; sequestering agents such as edetic acid and salts thereof, and metaphosphoric acid and salts thereof; beautifying ingredients such as arbutin, kojic acid and placenta extract; cell activators such as collagen, cycosaponin, royal jelly, fetal bovine serum extract, bovine spleen extract, bovine placenta extract, epichlestanol, ribonucleic acid; and besides ultraviolet absorbents, urea, coloring matter, various vitamins, sebum-secretion depressors, sebum-secretion accelerators, medicinally-effective ingredients, and perfume bases.

The skin cosmetic compositions according to the present invention can be prepared in accordance with any method known per se in the art, and formulated in the desired forms such as emulsions, dispersions, two-layer compositions, solutions, microemulsions and jelly. They may be provides as toilet waters, cosmetic emulsions, creams, essences, packs, foundations, etc.

No particular limitation is imposed on the proportions of the components (A) and (B) in the hair cosmetic compositions according to the present invention so far as the proportions fall within the above ranges. When incorporated in shampoos, their proportions are each preferably about 0.001 to 5%, based on the total weight of the composition. When incorporated in rinses, treatments, conditioners, and the like, their proportions are each preferably about 0.1 to 20%, based on the total weight of the composition. When incorporated in hair liquids, hair tonics and the like, their proportions are each preferably about 0.01 to 5%, based on the total weight of the composition.

In the hair cosmetic compositions according to the present invention, surfactants may be incorporated when the compositions are provided as shampoos, hair rinses, hair conditioners, hair treatments and the like. Examples of such surfactants include anionic surfactants, amphoteric surfactants, nonionic surfactants and cationic surfactants. As examples of the anionic surfactants and amphoteric surfactants, may be mentioned the same surfactants as those incorporated into the above-described skin cosmetic compositions.

Examples of the nonionic surfactants include polyoxyalkylene alkyl (or alkylene) ethers, polyoxyethylene alkyl phenyl ethers, polyoxypropylene alkyl (or alkylene) ethers, polyoxybutylene alkyl (or alkylene) ethers, nonionic surfactants obtained by adding ethylene oxide and propylene oxide, or ethylene oxide and butylene oxide, higher fatty acid alkanolamides or alkylene oxide adducts thereof, sucrose fatty acid esters, fatty acid monoglycerol esters, and alkylamine oxides.

Examples of the cationic surfactants include mono- or di-long-chain-alkyl quaternary ammonium salts.

Examples of counter ions to the anionic residues of these surfactants include alkali metal ions such as sodium and potassium, alkaline earth metal ions such as calcium and magnesium, ammonium ion, and alkanolamines having 1 to 3 alkanol groups having 2 or 3 carbon atoms (for example, monoethanolamine, diethanolamine, triethanolamine and triisopropanolamine). Examples of counter ions to the cationic residues include halogen ions such as chlorine, bromine and iodine, and metasulfate and saccharinate ions.

When used in the shampoos and the like, anionic surfactants such as alkyl ether sulfates, alkylsulfates and olefinsulfonates among these surfactants are particularly preferred as principal surfactants. Preferable examples thereof include sodium polyoxyethylene lauryl ether sulfate (average number of moles of ethylene oxide added: 2 to 3), triethanolamine laurylsulfate and sodium α-olefinsulfonate (average number of carbon atoms: 12 to 14).

When used in the shampoos and the like, these surfactants are incorporated in a proportion of 5 to 30%, preferably 10 to 20%, in total, based on the total weight of the composition. When used in the hair rinses, hair treatments, hair conditioners and the like, the nonionic or cationic surfactants are incorporated in a proportion of 0.1 to 50%, preferably 0.5 to 20%, based on the total weight of the composition.

When the hair cosmetic composition is provided as a hair rinse, hair treatment or hair conditioner, long-chain-alkyl quaternary ammonium salts, and oils and fats may be incorporated with a view toward imparting a more pleasant feel to the hair. Examples of the long-chain-alkyl quaternary ammonium salts include long-chain-alkyl quaternary ammonium salts represented by the following general formula (20):

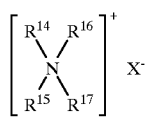

(20)

wherein one or two of $R^{14}$ to $R^{17}$ are linear or branched long-chain alkyl groups having 8 to 24 carbon atoms, the residual R groups are, independently, an alkyl or hydroxyalkyl group having 1 to 3 carbon atoms, or a benzyl group, and X⁻ is a halogen atom or an alkylsulfate group having 1 to 2 carbon atoms. These ammonium salts may be used either singly or in any combination thereof. Of the long-chain-alkyl quaternary ammonium salts represented by the general formula (20), those, in which the long-chain-alkyl group(s) are branched, are synthesized by using, as a raw material, a branched higher fatty acid or branched higher alcohol in accordance with a method known per se in the art. These raw materials may be either natural substances or synthetic products Examples of the natural raw materials include lanolin fatty acids such as iso-acids and anteisoacids, and terpene alcohols such as farnesol. Examples of the synthetic raw materials include oxo alcohols obtained by using an olefin in accordance with the oxo process, and Guerbet alcohols and 2-alkylalkanols obtained by using an alcohol or an aldehyde as a raw material in accordance with the Guerbet reduction or aldol condensation. In the case of, for example, an oxo alcohol, the branching rate of the higher alcohol formed is low when the raw material is an α-olefin. When the raw material is an inner olefin, the branching rate becomes higher. In the case of a branched olefin, the branching rate is 100%.

In the branched, long-chain-alkyl quaternary ammonium salts, the branched alkyl group is preferably a 2-methylalkyl group represented by the general formula (21):

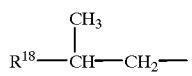

(21)

wherein $R^{18}$ is a linear alkyl group having 5 to 13 carbon atoms. Preferable specific examples thereof include 2-methyloctyl, 2-methyldecyl, 2-methylundecyl, 2-methyldodecyl, 2-methyltridecyl, 2-methyltetradecyl and 2-methylheptadecyl. These 2-methylalkyl groups are usually derived from their corresponding oxo alcohols. Such an oxo alcohol is generally obtained as a mixture with a linear alcohol.

Examples of the branched, long-chain-alkyl quaternary ammonium salts having these branched alkyl groups include alkyltrimethylammonium chloride, dialkyldimethylammonium chloride, alkyldimethylbenzylammonium chloride, alkyltrimethylammonium bromide, alkyltrimethylammonium metosulfate and dialkylmethylhydroxymethylammonium chloride. Of these, those having the 2-methylalkyl group(s) represented by the formula (21) are particularly preferred. Examples thereof include branched, mono-long-chain-alkyl quaternary ammonium salts such as 2-methyldecyltrimethylammonium chloride, 2-methyldodecyltrimethylammonium chloride and 2-methyltetradecyltrimethylammonium chloride; branched, di-long-chain-alkyl quaternary ammonium salts one of the long-chain-alkyl groups of which is branched, such as 2-methyldecylundecyldimethylammonium chloride, 2-methyl-dodecyltridecyldimethylammonium chloride and 2-methyl-tetradecylpentadecyldimethviammonium chloride; and branched, di-long-chain-alkyl quaternary ammonium salts both long-chain-alkyl groups of which are branched, such as di(2-methyldecyl)dimethylammonium chloride, di(2-methyldodecyl)dimethylammonium chloride and di(2-methyltetradecyl)dimethylammonium chloride.

Examples of the linear long-chain alkyl groups include decyl, undecyl, dodecyl, tridecyl, tetradecyl, pentadecyl, hexadecyl, octadecyl, and eicosanyl groups.

As the oils and fats, there may be used those routinely employed. Examples thereof include liquid paraffin, glycerides, higher alcohols, lanolin derivatives, esters and higher fatty acids. As the glycerides, monoglycerides derived from saturated or unsaturated and linear or branched fatty acids having 12 to 24 carbon atoms are used. Among these oils and fats, higher alcohols having a linear or branched alkyl or alkenyl groups having 12 to 26 carbon atoms are particularly preferred. Preferable specific examples thereof include cetyl alcohol, stearyl alcohol, arachidic alcohol, behenyl alcohol, caranerbil alcohol and ceryl alcohol.

Preferable proportions of these long-chain-alkyl quaternary ammonium salts, and oils and fats to be incorporated are 0.01 to 20% and 0.1 to 30%, respectively, based on the total weight of the composition.

When the hair cosmetic composition is provided as a hair liquid or hair tonic, a nonionic surfactant may be used in combination with the components (A) and (B) Examples of this nonionic surfactant include the same surfactants as those incorporated in the above-described skin cosmetic compositions.

It is preferable to incorporate the nonionic surfactant in a proportion of 0.01 to 20%, particularly 0.1 to 5%, based on the total weight of the composition.

The hair cosmetic compositions according to the present invention can be formulated in the forms of aqueous solutions, ethanolic solutions, emulsions, suspensions, gels, solids, aerosol, powders and the like, and no particular limitation is imposed on the forms thereof. Besides the above components, the same components as those incorporated in the above-described skin cosmetic compositions may be incorporated as cosmetic ingredients as needed.

Other features of the invention will become apparent in the course of the following descriptions of exemplary embodiments which are given for illustration of the invention and are not intended to be limiting thereof.

EXAMPLES

Vegetable extracts of the component (B) were prepared in accordance with the following processes to give a dry solid content of 0.1 to 20%. In the following examples, the vegetable extracts obtained in these Preparation Examples 1–8 were used.

Preparation Example 1

Preparation Process of Hamamelis Extract

Added to 100 grams of a dry ground product of leaves and bark of hamamelis were 1,000 ml of 50 v/v % aqueous ethanol to conduct extraction for 3 days while sometimes stirring the mixture at room temperature. The resultant extract was filtered, and the filtrate was left at rest for 3 days at 5° C. and then filtered again, thereby obtaining a supernatant.

Preparation Example 2

Preparation Process of Peony Extract

An extract was prepared in the same manner as in Preparation Example 1 except that a dry ground product of root and bark of peony was used in place of the dry ground product of hamamelis.

Preparation Example 3

Preparation Process of Agrimony Extract

An extract was prepared in the same manner as in Preparation Example 1 except that a dry ground product of the whole of agrimony was used in place of the dry ground product of hamamelis.

Preparation Example 4

Preparation Process of Japanese Catalpa Extract

An extract was prepared in the same manner as in Preparation Example 1 except that a dry ground product of fruits of Japanese catalpa was used in place of the dry ground product of hamamelis.

Preparation Example 5

Preparation Process of Hiba Arborvitae Extract

An extract was prepared in the same manner as in Preparation Example 1 except that a dry ground product of leaves, bark and root of hiba arborvitae was used in place of the dry ground product of hamamelis.

Preparation Example 6

Preparation Process of HORUTOSO Extract

An extract was prepared in the same manner as in Preparation Example 1 except that a dry ground product of seeds or the whole of HORUTOSO was used in place of the dry ground product of hamamelis.

Preparation Example 7

Preparation Process of *Isodon Japonicus Hara* Extract

An extract was prepared in the same manner as in Preparation Example 1 except that a dry ground product of the whole of *Isodon japonicus Hara* was used in place of the dry ground product of hamamelis.

Preparation Example 8

Preparation Process of KIJITSU Extract

An extract was prepared in the same manner as in Preparation Example 1 except that a dry ground product of KIJITSU was used in place of the dry ground product of hamamelis.

The evaluation methods as to effects for the improvement of skin roughness in the present invention are described below.

Testing Methods

Chosen as volunteers in winter were 10 women of 20 to 50 years of age who had-skin roughness on their both cheeks. Different external skin-care preparations were applied separately to the left and right cheeks of each volunteer for 2 weeks- On the day following the completion of the two-week application test, tests were conducted with respect to the following properties.

(1) Skin Conductance:

After washing the face with warm water of 37° C., each volunteer was allowed to rest for 20 minutes in a room which was air-conditioned at 20° C. and 40% humidity. The water content of her horny layer was measured by a skin conductance neter (manufactured by IBS Company). A smaller conductance value indicates greater skin roughness. Conductance values of 5 and smaller indicate severe skin roughness. On the contrary, no substantial skin roughness is observed where this value is 20 or greater.

(2) Score of Skin Roughness:

Skin roughness was observed visually and ranked in accordance with the following standard shown. Each score was indicated by an average value.

0: No skin roughness was observed;
1: Slight skin roughness was observed;
2: Skin roughness was observed;
3: Rather severe skin roughness was observed;
4: Severe skin roughness was observed.

Example 1

O/W type creams having the following composition were prepared to evaluate their effects for the improvement of skin roughness by continuous application.

The structures of amide derivatives used, and polyhydric alcohols used as well as their proportions incorporated are shown in Tables 1–4, and the evaluation results as to the effects for the improvement of skin roughness are shown in Table 5.

TABLE 1

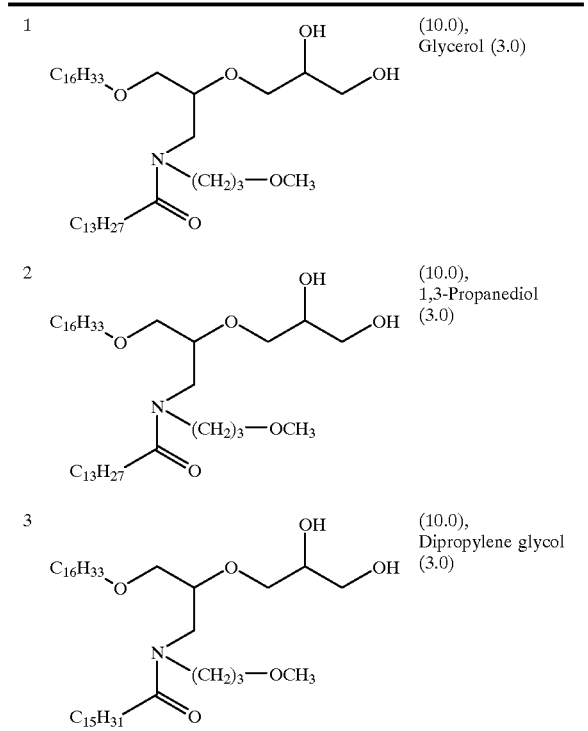

TABLE 1-continued
| | | |
|---|---|---|
| 4 | 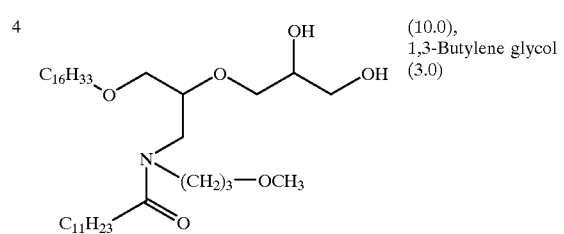 | (10.0), 1,3-Butylene glycol (3.0) |
| 5 | 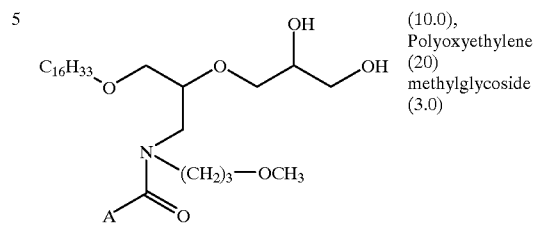 (A is a mixture of $C_{14}H_{29}$, $C_{16}H_{33}$ and $C_{18}H_{37}$) | (10.0), Polyoxyethylene (20) methylglycoside (3.0) |
TABLE 2
| | | |
|---|---|---|
| 6 | 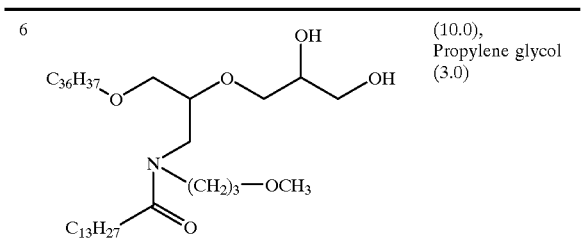 | (10.0), Propylene glycol (3.0) |
| 7 | 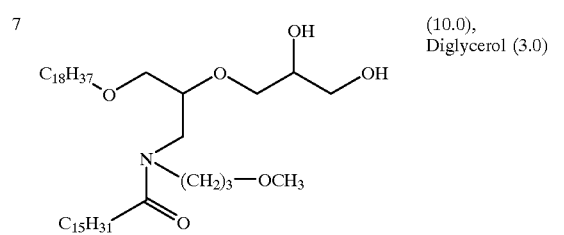 | (10.0), Diglycerol (3.0) |
| 8 | 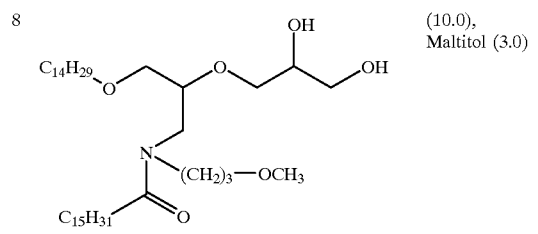 | (10.0), Maltitol (3.0) |
| 9 | 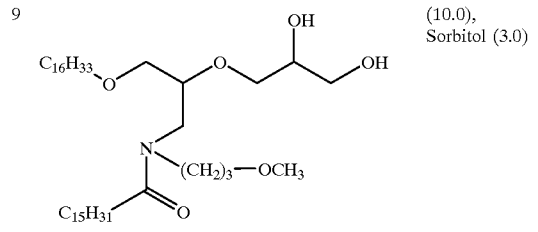 | (10.0), Sorbitol (3.0) |
TABLE 2-continued
| | | |
|---|---|---|
| 10 | 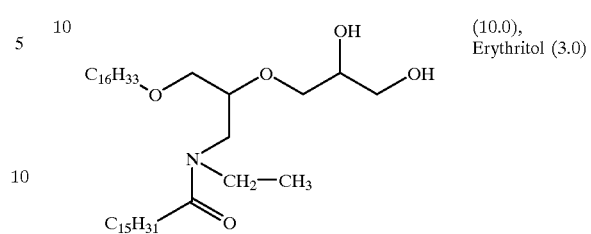 | (10.0), Erythritol (3.0) |
TABLE 3
| | | |
|---|---|---|
| 11 | 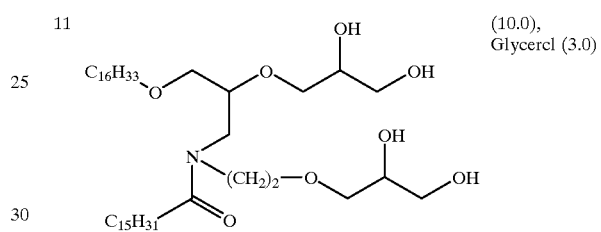 | (10.0), Glycerol (3.0) |
| 12 | 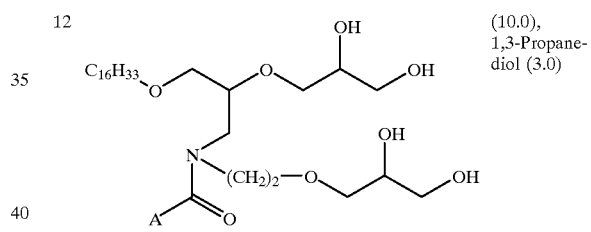 (A is a mixture of $C_{14}H_{29}$, $C_{16}H_{33}$ and $C_{18}H_{37}$) | (10.0), 1,3-Propanediol (3.0) |
| 13 | 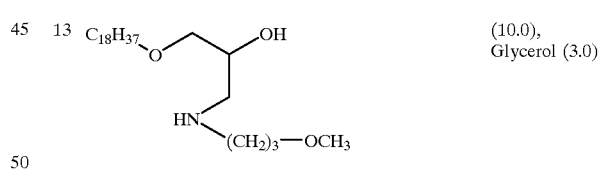 | (10.0), Glycerol (3.0) |
| 14 | 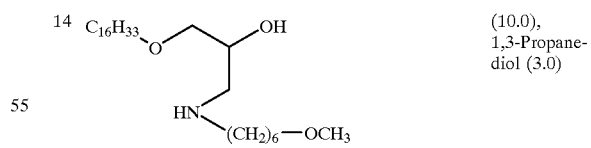 | (10.0), 1,3-Propanediol (3.0) |
| 15 | 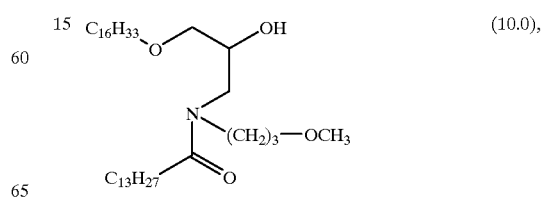 | (10.0), |

TABLE 3-continued

16

$C_{16}H_{33}$—O—CH(—O—CH$_2$—CH(OH)—CH$_2$OH)—CH$_2$—N(—(CH$_2$)$_3$—OCH$_3$)—C(=O)—C$_{13}$H$_{27}$ (10.0)

17 Glycerol (3.0)
18 Glucose (3.0)

Numerals in parentheses mean amounts (%) incorporated.
1–14: Invention products; 15–18: Comparative products.

| (Composition) | | (%) |
|---|---|---|
| (1) | Amide derivative (see Table 1–4) | See Tables 1–4 |
| (2) | Polyhydric alcohol (see Table 1–4) | See Tables 1–4 |
| (3) | Citric acid | 1.0 |
| (4) | Polyoxyethylene (10) hardened castor oil | 1.0 |
| (5) | Sorbitan monostearate | 0.5 |
| (6) | Sodium stearoyl methyltaurine | 0.5 |
| (7) | Sodium polyoxyethylene lauryl ether phosphate | 0.5 |
| (8) | Cholesterol | 1.3 |
| (9) | Cetostearyl alcohol | 2.0 |
| (10) | Cholesteryl isostearate | 1.0 |
| (11) | Squalane | 2.0 |
| (12) | Neopentylglycol dicaprate | 8.0 |
| (13) | Methylpolysiloxane*1 | 4.0 |
| (14) | Cyclic silicone*2 | 4.0 |
| (15) | Antiseptic | q.s. |
| (16) | Purified water | Balance |
| (17) | Ethanol | 3.0 |
| (18) | Perfume base | q.s. |
| | Total | 100.0 |

*1: Silicone KF96A (6 cs), product of Shin-Etsu Chemical Co., Ltd.
*2: Silicone SH-244, SH-245 or a 3:2 (by weight) mixture of SH-244 and SH-245, product of Dow Corning Toray Silicone Co., Ltd.

Preparation Process

The oil-phase components [(1), (4), (5), (7) to (14); the component (2) may be included in the water phase according to the compound] were heated to 80° C. to melt them. The water-phase components [(3), (6), (15), (16)], which had been heated to 80° C. were added to the above molten oil-phase components with stirring to emulsify them. The resultant emulsion was then cooled to 50° C. with stirring. The components (17) and (18) were then added to the emulsion, and the resultant mixture was further cooled to room temperature with stirring, thereby obtaining an O/W type cream.

TABLE 5

| | No. | Skin conductance | Score of skin roughness |
|---|---|---|---|
| Invention product | 1 | 40 ± 2.7 | 0.4 ± 0.3 |
| | 2 | 39 ± 5.1 | 0.5 ± 0.2 |
| | 3 | 35 ± 3.3 | 0.6 ± 0.2 |
| | 4 | 37 ± 2.2 | 0.6 ± 0.4 |
| | 5 | 33 ± 4.1 | 0.4 ± 0.3 |
| | 6 | 30 ± 2.7 | 0.5 ± 0.3 |
| | 7 | 35 ± 3.8 | 0.7 ± 0.2 |
| | 8 | 30 ± 2.1 | 0.4 ± 0.2 |
| | 9 | 30 ± 3.4 | 0.4 ± 0.2 |
| | 10 | 28 ± 3.8 | 0.6 ± 0.3 |
| | 11 | 35 ± 4.7 | 0.5 ± 0.3 |
| | 12 | 38 ± 2.5 | 0.7 ± 0.3 |
| | 13 | 30 ± 3.4 | 0.8 ± 0.4 |
| | 14 | 30 ± 4.1 | 0.9 ± 0.4 |
| Comparative product | 15 | 16 ± 3.4 | 1.5 ± 0.6 |
| | 16 | 17 ± 4.1 | 1.4 ± 0.6 |
| | 17 | 10 ± 2.7 | 2.2 ± 0.8 |
| | 18 | 8 ± 1.9 | 2.9 ± 0.7 |

As apparent from Table 5, the compositions according to the present invention, in which the amide derivative (A) and the polyhydric acohol (B-1) were incorporated, exhibited excellent water-retaining effects on the horny layer and skin roughness-preventing effects.

Example 2

W/O Type Cream

A W/O type cream having the following composition was prepared.

| (Composition) | | (%) |
|---|---|---|
| (1) | Amide derivative (the same compound as Compound No. 1 in Table 1) | 3.5 |
| (2) | Citric acid | 0.5 |
| (3) | Glycerol | 1.0 |
| (4) | Cholesterol | 0.5 |
| (5) | Cholesteryl isostearate | 0.5 |
| (6) | Polyether-modified silicone*3 | 2.0 |
| (7) | Cyclic silicone*4 | 20.0 |
| (8) | Methylphenylpolysiloxane*5 | 5.0 |
| (9) | Magnesium sulfate | 0.5 |
| (10) | Acid polysaccharide*6 | 5.0 |
| (11) | Purified water | Balance |
| (12) | Antiseptic | q.s. |
| (13) | Perfume base | q.s. |
| | Total | 100.0 |

*3: Silicone KF-6015, product of Shin-Etsu Chemical Co., Ltd.
*4: A 3:2 (by weight) mixture of Silicone SH-244 and SH-245, product of Dow Corning Toray Silicone Co., Ltd.
5*: Silicone SF-557, product of Dow Corning Toray Silicone Co., Ltd.
6*: An acid polysaccharide derived from the callus of tuberose prepared in accordance with Example 1 of Japanese Patent Application Laid-open No. 10997/1989.

Preparation Process

The oil-phase components [(1), (4) to (6), (8)] were heated to 80° C. to melt them. The water-phase components [(2), (3), (9) to (12)], which had been heated to 80° C., were added to the above molten oil-phase components with stirring to emulsify them. The resultant emulsion was then cooled to 50° C. with stirring. The components (7) and (13) were then added to the emulsion, and the resultant mixture was further cooled to room temperature with stirring, thereby obtaining a W/O type cream.

Example 3

O/W Type Moisturizing Lotion

An O/W type moisturizing lotion having the following composition was prepared in accordance with a method known per se in the art.

| (Composition) | | (%) |
|---|---|---|
| (1) | Amide derivative (the same compound as Compound No. 1 in Table 1) | 3.0 |
| (2) | Cholesterol | 0.5 |
| (3) | 1-(2-Hydroxyethylamino)-3-isostearyloxy-2-propanol*7 | 0.2 |
| (4) | 2-(2-Hydroxyethoxy) ethylguanidine*8 | 0.5 |
| (5) | Cetyl alcohol | 1.0 |
| (6) | Vaseline | 2.0 |
| (7) | Squalane | 5.0 |
| (8) | Dimethylpolysiloxane (6 cSt) | 2.0 |
| (9) | Glycerol | 4.0 |
| (10) | 1,3-Propanediol | 2.0 |
| (11) | Polyoxyethylene (20) sorbitan monooleate | 0.5 |
| (12) | Sorbitan monostearate | 0.3 |
| (13) | Acid polysaccharide*6 | 5.0 |
| (14) | Cholesteryl mono-n-hexadecenylsuccinate | 1.0 |
| (15) | Stearyl glycyrrhetinate | 1.0 |
| (16) | Tocopherol | 1.0 |
| (17) | Succinic acid | 0.55 |
| (18) | Sodium dihydrogenphosphate | 0.9 |
| (19) | Carboxyvinyl polymer*9 | 0.15 |
| (20) | Potassium hydroxide | 0.045 |
| (21) | Purified water | Balance |
| | Total | 100.0 |

*6: An acid polysaccharide derived from the callus of tuberose prepared in accordance with Example 1 of Japanese Patent Application Laid-open No. 10997/1989.
*7: Prepared in accordance with Synthetic Example 3 of Japanese Patent Application Laid-open No. 17849/1995, which is incorporated herein by reference
*8: Prepared in accordance with Example 1 of Japanese Patent Application Laid-Open No. 170628/1995, which is incorporated herein by reference.
*9: Carbopol 940, product of Goodrich Company.

Example 4

Moisturizing Essence

A moisturizing essence having the following composition was prepared in accordance with a method known per se in the art.

| (Composition) | | (%) |
|---|---|---|
| (1) | Acid polysaccharide*6 | 0.20 |
| (2) | Xanthan gum | 0.50 |
| (3) | Ethanol | 6.40 |
| (4) | Amide derivative (the same compound as Compound No. 1 in Table 1) | 0.10 |
| (5) | 1-(2-Hydroxyethylamino)-3-isostearyloxy-2-propanol*7 | 0.20 |
| (6) | 2- (2-Hydroxyethoxy)ethylguanidine*8 | 0.10 |
| (7) | Urea | 2.50 |
| (8) | ε-Aminocapronic acid | 0.83 |
| (9) | Succinic acid | 1.50 |
| (10) | Glycerol | 12.00 |
| (11) | Dipropylene glycol | 3.00 |
| (12) | Methyl p-oxybenzoate | 0.20 |
| (13) | Polyoxyethylene isocetyl ether (20 E.O.) | 0.30 |
| (14) | Tannic acid | 0.02 |
| (15) | Glycinebetaine | 0.50 |
| (16) | Antiseptic | 0.10 |
| (17) | Purified water | Balance |
| | Total | 100.0 |

*6: An acid polysaccharide derived from the callus of tuberose prepared in accordance with Example 1 of Japanese Patent Application Laid-Open No. 10997/1989
*7: Prepared in accordance with Synthetic Example 3 of Japanese Patent Application Laid-open No. 17849/1995.
*8: Prepared in accordance with Example 1 of Japanese Patent Application Laid-Open No. 170628/1995.

All the cosmetic compositions obtained in Examples 1–4 could enhance the water-retaining ability of the horny layer and had excellent effects for the improvement of skin roughness.

Example 5

O/W type creams having the following composition were prepared to evaluate their effects for the improvement of skin roughness by continuous application in the same manner as described above.

The structures of amide derivatives used, and organic acids or salts thereof and polyhydric alcohols used as well as their proportions incorporated are shown in Tables 6–9, and the evaluation results as to the effects for the improvement of skin roughness are shown in Table 10.

TABLE 6

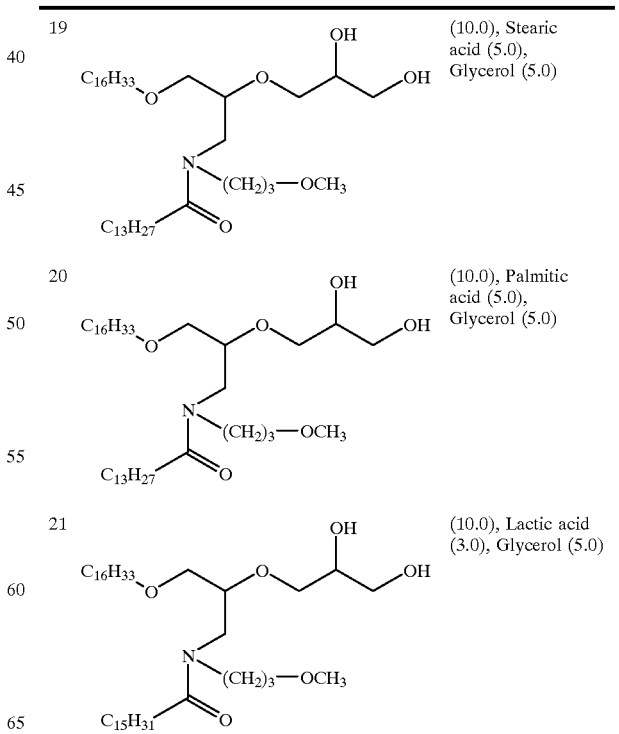

TABLE 6-continued

| | Structure | Components |
|---|---|---|
| 22 | C16H33-O-CH2-CH(O-CH2-CH(OH)-CH2-OH)-CH2-N((CH2)3-OCH3)(C(=O)-C11H23) | (10.0), Na lactate (3.0), 1,3-Butylene glycol (5.0) |
| 23 | C16H33-O-CH2-CH(O-CH2-CH(OH)-CH2-OH)-CH2-N((CH2)3-OCH3)(C(=O)-A) | (10.0), Citric acid (3.0), 1,3-Butylene glycol (5.0) |

(A is a mixture of $C_{14}H_{29}$, $C_{16}H_{33}$ and $C_{18}H_{37}$)

TABLE 7

| | Structure | Components |
|---|---|---|
| 24 | C18H37-O-CH2-CH(O-CH2-CH(OH)-CH2-OH)-CH2-N((CH2)3-OCH3)(C(=O)-C13H27) | (10.0), Na citrate (3.0), 1,3-Butylene glycol (5.0) |
| 25 | C18H37-O-CH2-CH(O-CH2-CH(OH)-CH2-OH)-CH2-N((CH2)3-OCH3)(C(=O)-C15H31) | (10.0), Glycolic acid (3.0), Sorbit (5.0) |
| 26 | C14H29-O-CH2-CH(O-CH2-CH(OH)-CH2-OH)-CH2-N((CH2)3-OCH3)(C(=O)-C15H31) | (10.0), Succinic acid (3.0), Sorbit (5.0) |
| 27 | C16H33-O-CH2-CH(O-CH2-CH(OH)-CH2-OH)-CH2-N((CH2)3-OCH3)(C(=O)-C15H31) | (5.0), aspartic acid (3.0), Sorbit (3.0) |

TABLE 7-continued

| | Structure | Components |
|---|---|---|
| 28 | C16H33-O-CH2-CH(O-CH2-CH(OH)-CH2-OH)-CH2-N(CH2-CH3)(C(=O)-C15H31) | (5.0), Sterol derivative*10 (3.0), Dipropylene glycol (5.0) |

TABLE 8

| | Structure | Components |
|---|---|---|
| 29 | C16H33-O-CH2-CH(O-CH2-CH(OH)-CH2-OH)-CH2-N((CH2)2-O-CH2-CH(OH)-CH2-OH)(C(=O)-C15H31) | (5.0), 2-Hydroxy-octanoic acid (3.0), Polyoxy-ethylene methyl-glucoside (5.0) |
| 30 | C16H33-O-CH2-CH(O-CH2-CH(OH)-CH2-OH)-CH2-N((CH2)2-O-CH2-CH(OH)-CH2-OH)(C(=O)-A) | (5.0), Linolic acid (3.0), 1,3-Propylene glycol (5.0) |

(A is a mixture of $C_{14}H_{29}$, $C_{16}H_{33}$ and $C_{18}H_{37}$)

| | Structure | Components |
|---|---|---|
| 31 | C18H37-O-CH2-CH(OH)-CH2-NH-(CH2)3-OCH3 | (5.0), γ-Aminobutyric acid (3.0) |
| 32 | C16H33-O-CH2-CH(OH)-CH2-NH-(CH2)6-OCH3 | (5.0), Na glutamate (3.0) |
| 33 | C16H33-O-CH2-CH(OH)-CH2-N((CH2)3-OCH3)(C(=O)-C13H27) | (5.0), Glycerol (1.0) |

| (Composition) | | (%) |
|---|---|---|
| (1) | Amide derivative (see Table 6–9) | See Tables 6–9 |
| (2) | Organic acid or a salt thereof (see Table 6–9) | See Tables 6–9 |
| (3) | Polyhydric alcohol (see Table 6–9) | See Tables 6–9 |
| (4) | Polyoxyethylene (10) hardened castor oil | 1.0 |
| (5) | Sorbitan monostearate | 0.5 |
| (6) | Sodium stearoyl methyltaurine | 0.5 |

-continued

| (Composition) | | (%) |
|---|---|---|
| (7) | Sodium polyoxyethylene lauryl ether phosphate | 0.5 |
| (8) | Cholesterol | 1.3 |
| (9) | Cetostearyl alcohol | 2.0 |
| (10) | Cholesteryl isostearate | 1.0 |
| (11) | Squalane | 2.0 |
| (12) | Neopentylglycol dicaprate | 8.0 |
| (13) | Methylpolysiloxane*1 | 4.0 |
| (14) | Cyclic silicone*2 | 4.0 |
| (15) | Antiseptic | q.s. |
| (16) | Purified water | Balance |
| (17) | Ethanol | 3.0 |
| (18) | Perfume base | q.s. |
| | Total | 100.0 |

*1: Silicone KF96A (6 cs), product of Shin-Etsu Chemical Co., Ltd.
*2: Silicone SH-244, SH-245 or a 3:2 (by weight) mixture of SH-244 and SH-245, product of Dow Corning Toray Silicone Co., Ltd.

TABLE 9

34  $C_{16}H_{33}$–O–CH(–O–CH$_2$–epoxide)–CH$_2$–N(–(CH$_2$)$_4$–OCH$_3$)–C(=O)–$C_{13}H_{27}$   (5.0), Glycerol (1.0)

35 Stearic acid (3.0)
36 Citric acid (3.0)

Numerals in parentheses mean amounts (%) incorporated.
19–32: Invention products;
33–36: Comparative products.
*$^{10}$: A compound of the general formula (5) in which 1 is 2, and $R^z$ is cholesteryl.

Preparation Process

The oil-phase components [(1), (4), (5), (7) to (14); the component (2) may be included in the water phase according to the compound] were heated to 80° C. to melt them. The water-phase components C(3), (6), (15), (16)], which had been heated to 80° C., were added to the above molten oil-phase components with stirring to emulsify them. The resultant emulsion was then cooled to 50° C. with stirring. The components (17) and (18) were then added to the emulsion, and the resultant mixture was further cooled to room temperature with stirring, thereby obtaining an O/W type cream.

TABLE 10

| | No. | Skin conductance | Score of skin roughness |
|---|---|---|---|
| Invention product | 19 | 44 ± 5.2 | 0.4 ± 0.2 |
| | 20 | 33 ± 4.7 | 0.6 ± 0.3 |
| | 21 | 37 ± 2.3 | 0.7 ± 0.4 |
| | 22 | 28 ± 3.0 | 0.7 ± 0.3 |
| | 23 | 40 ± 3.7 | 0.5 ± 0.3 |
| | 24 | 35 ± 2.5 | 0.6 ± 0.2 |
| | 25 | 29 ± 2.4 | 0.7 ± 0.4 |
| | 26 | 36 ± 2.9 | 0.4 ± 0.3 |
| | 27 | 41 ± 4.0 | 0.4 ± 0.2 |
| | 28 | 29 ± 5.4 | 0.6 ± 0.3 |
| | 29 | 45 ± 3.6 | 0.4 ± 0.2 |
| | 30 | 38 ± 4.1 | 0.5 ± 0.3 |
| | 31 | 26 ± 3.0 | 0.9 ± 0.4 |
| | 32 | 25 ± 2.8 | 0.8 ± 0.3 |
| Comparative product | 33 | 19 ± 3.5 | 1.4 ± 0.5 |
| | 34 | 15 ± 2.3 | 1.3 ± 0.6 |
| | 35 | 8 ± 1.2 | 2.5 ± 0.8 |
| | 36 | 10 ± 1.9 | 3.0 ± 0.5 |

Example 6

A W/O type cream having the following composition was prepared. This cream had excellent effects in improving the water-retaining ability of the horny layer, and preventing and curing skin roughness.

| (Composition) | | (%) |
|---|---|---|
| (1) | Amide derivative (the same compound as Compound No. 19 in Table 6) | 3.5 |
| (2) | Citric acid | 0.5 |
| (3) | Glycerol | 1.0 |
| (4) | Cholesterol | 0.5 |
| (5) | Cholesteryl isostearate*3 | 0.5 |
| (6) | Polyether-modified silicone | 2.0 |
| (7) | Cyclic silicone*4 | 20.0 |
| (8) | Methylphenylpolysiloxane*5 | 5.0 |
| (9) | Magnesium sulfate | 0.5 |
| (10) | Purified water | Balance |
| (11) | Antiseptic | q.s. |
| (12) | Perfume base | q.s. |
| | Total | 100.0 |

*3Silicone KF-6015, product of Shin-Etsu Chemical Co., Ltd.
*4A 3:2 (by weight) mixture of Silicone SH-244 and SH-245, product of Dow Corning Toray Silicone Co., Ltd.
*5Silicone SF-557, product of Dow Corning Toray Silicone Co., Ltd.

Preparation Process

The oil-phase components [(1), (4) to (6), (8)] were heated to 80° C. to melt them The water-phase components [(2), (3), (9) to (11)], which had been heated to 80° C., were added to the above molten oil-phase components with stirring to emulsify them. The resultant emulsion was then cooled to 50° C. with stirring. The components (7) and (12) were then added to the emulsion, and the resultant mixture was further cooled to room temperature with stirring, thereby obtaining a W/O type cream.

Example 7

A hair tonic having the following composition was prepared. This hair tonic could improve the water-retaining ability of the horny layer, protect the hair and head skin and gave a pleasant feel to the hair.

| (Composition) | | (%) |
|---|---|---|
| (1) | Amide derivative (the same compound as Compound No. 19 in Table 6) | 1.0 |

-continued (Composition)

| | | (%) |
|---|---|---|
| (2) | Sterol derivative*10 | 1.0 |
| (3) | 1,3-Butylene glycol | 3.0 |
| (4) | Aluminum pyrrolidonecarboxylate | 0.5 |
| (5) | Ethanol | 55.0 |
| (6) | Purified water | Balance |
| (7) | Perfume base | q.s. |
| | Total | 100.0 |

*10 A compound of the general formula (5) in which 1 is 2, and $R^2$ is cholesteryl.

Preparation Process

The components (1) and (2) were uniformly dispersed in the component (6) under stirring. The components (3), (4), (5) and (7) were then added to the resultant dispersion, and the mixture was thoroughly stirred to prepare a hair tonic.

Example 8

O/W type creams having the following composition were prepared to evaluate their effects for the prevention of the formation of wrinkles upon their use by the following method.

The structures of amide derivatives used and incorporated components such as vegetable extracts (those obtained in Preparation Examples 1–8) as well as their proportions (%) incorporated are shown in Tables 11–14 (37 to 50: invention products; 51–54: comparative products), and the evaluation results as to the effects for the prevention of formation of wrinkles are shown in Table 15.

TABLE 11

| 37 | [Structure: $C_{16}H_{33}$–O–CH$_2$–CH(O–CH$_2$–CH(OH)–CH$_2$OH)–CH$_2$–N($C_{13}H_{27}$–C(=O)–)–(CH$_2$)$_3$–OCH$_3$] | (10.0), Hamamelis extract (dry solid 1.5%) (1.0), Acid polysaccharide*6 (1.0) |
| 38 | [Structure: $C_{16}H_{33}$–O–CH$_2$–CH(O–CH$_2$–CH(OH)–CH$_2$OH)–CH$_2$–N($C_{13}H_{27}$–C(=O)–)–(CH$_2$)$_3$–OCH$_3$] | (10.0), Hiba arborvitae extract (dry solid 1.5%) (1.0), Cholesteryl isostearate (1.0) |
| 39 | [Structure: $C_{16}H_{33}$–O–CH$_2$–CH(O–CH$_2$–CH(OH)–CH$_2$OH)–CH$_2$–N($C_{15}H_{31}$–C(=O)–)–(CH$_2$)$_3$–OCH$_3$] | (10.0), Agrimony extract (dry solid 1.0%) (1.0), Stearyl glycyrrhetinate (0.1) |

TABLE 11-continued

| 40 | [Structure: $C_{16}H_{33}$–O–CH$_2$–CH(O–CH$_2$–CH(OH)–CH$_2$OH)–CH$_2$–N($C_{11}H_{23}$–C(=O)–)–(CH$_2$)$_3$–OCH$_3$] | (10.0), Japanese catalpa extract (dry solid 1.0%) (1.0), Tocopherol (0.1) |
| 41 | [Structure: $C_{16}H_{33}$–O–CH$_2$–CH(O–CH$_2$–CH(OH)–CH$_2$OH)–CH$_2$–N(A–C(=O)–)–(CH$_2$)$_3$–OCH$_3$] | (10.0), Peony extract (dry solid 1.0%) (1.0), Cholesterol (1.0) |

(A is a mixture of $C_{14}H_{29}$, $C_{16}H_{33}$ and $C_{18}H_{37}$)

*6: An acid polysaccharide derived from the callus of tuberose prepared in accordance with Example 1 of Japanese Patent Application Laid-Open No. 10997/1989.

TABLE 12

| 42 | [Structure: $C_{18}H_{37}$–O–CH$_2$–CH(O–CH$_2$–CH(OH)–CH$_2$OH)–CH$_2$–N($C_{13}H_{27}$–C(=O)–)–(CH$_2$)$_3$–OCH$_3$] | (10.0), HORUTOSO extract (dry solid 1.0%) (1.0), ε-Amino-carponic acid (5.0) |
| 43 | [Structure: $C_{18}H_{37}$–O–CH$_2$–CH(O–CH$_2$–CH(OH)–CH$_2$OH)–CH$_2$–N($C_{15}H_{31}$–C(=O)–)–(CH$_2$)$_3$–OCH$_3$] | (10.0), KIJITSU extract (dry solid 1.0%) (1.0), Tannic acid (0.1) |
| 44 | [Structure: $C_{14}H_{29}$–O–CH$_2$–CH(O–CH$_2$–CH(OH)–CH$_2$OH)–CH$_2$–N($C_{15}H_{31}$–C(=O)–)–(CH$_2$)$_3$–OCH$_3$] | (10.0), *Isodon japonicus Hara* extract (dry solid 1.5%) (1.0), Cholesteryl alkenyl-succinate (1.0) |
| 45 | [Structure: $C_{16}H_{33}$–O–CH$_2$–CH(O–CH$_2$–CH(OH)–CH$_2$OH)–CH$_2$–N($C_{15}H_{31}$–C(=O)–)–(CH$_2$)$_3$–OCH$_3$] | (10.0), Hamamelis extract (dry solid 1.5%) (1.0), Glycyrrhetinic acid (0.1) |

TABLE 12-continued

| # | Structure | Additives |
|---|---|---|
| 46 | C$_{16}$H$_{33}$-O-CH$_2$-CH(O-CH$_2$-CH(OH)-CH$_2$OH)-CH$_2$-N(CH$_2$-CH$_3$)-C(=O)-C$_{15}$H$_{31}$ | (10.0), Peony extract (dry solid 1.0%) (1.0), Ascorbic acid (0.1) |

TABLE 13

| # | Structure | Additives |
|---|---|---|
| 47 | C$_{16}$H$_{33}$-O-CH$_2$-CH(O-CH$_2$-CH(OH)-CH$_2$OH)-CH$_2$-N((CH$_2$)$_2$-O-CH$_2$-CH(OH)-CH$_2$OH)-C(=O)-C$_{15}$H$_{31}$ | (10.0), Agrimony extract (dry solid 1.0%) (1.0), Carotene (0.1) |
| 48 | C$_{16}$H$_{33}$-O-CH$_2$-CH(O-CH$_2$-CH(OH)-CH$_2$OH)-CH$_2$-N((CH$_2$)$_2$-O-CH$_2$-CH(OH)-CH$_2$OH)-C(=O)-A  (A is a mixture of C$_{14}$H$_{29}$, C$_{16}$H$_{33}$ and C$_{18}$H$_{37}$) | (10.0), Japanese catalpa extract (dry solid 1.0%) (1.0), Cholesteryl isostearate (1.0) |
| 49 | C$_{18}$H$_{37}$-O-CH$_2$-CH(OH)-CH$_2$-NH-(CH$_2$)$_3$-OCH$_3$ | (10.0), Hamamelis extract (dry solid 1.5%) (3.0) |
| 50 | C$_{16}$H$_{33}$-O-CH$_2$-CH(OH)-CH$_2$-NH-(CH$_2$)$_6$-OCH$_3$ | (10.0), *Isodon japonicus Hara* extract (dry solid 1.5%) (1.0) |
| 51 | C$_{16}$H$_{33}$-O-CH$_2$-CH(OH)-CH$_2$-N((CH$_2$)$_3$-OCH$_3$)-C(=O)-C$_{13}$H$_{27}$ | (10.0) |

TABLE 14

| 52 | *Hiba arborvitae* extract (dry solid 1.5%) (1.0) |
| 53 | Cholesterol (1.0) |
| 54 | Glycyrrhetinic acid (0.1) |
| 55 | Carotene (0.1) |

(Composition)

|   |   | (%) |
|---|---|---|
| (1) | Amide derivative (see Table 11–14) | See Tables 11–14 |
| (2) | Vegetable extract, etc. (see Table 11–14) | See Tables 11–14 |
| (3) | Glycerol | 1.0 |
| (4) | Polyoxyethylene (10) hardened castor oil | 1.0 |
| (5) | Sorbitan monostearate | 0.5 |
| (6) | Sodium stearoyl methyltaurine | 0.5 |
| (7) | Sodium polyoxyethylene lauryl ether phosphate | 0.5 |
| (8) | Cetostearyl alcohol | 2.0 |
| (9) | Squalane | 2.0 |
| (10) | Neopentylglycol dicaprate | 8.0 |
| (11) | Methylpolysiloxane*1 | 4.0 |
| (12) | Cyclic silicone*2 | 4.0 |
| (13) | Antiseptic | q.s. |
| (14) | Purified water | Balance |
| (15) | Ethanol | 3.0 |
| (16) | Perfume base | q.s. |
|   | Total | 100.0 |

*1: Silicone KF96A (6 cs), product or Shin-Etsu Chemical Co., Ltd
*2: Silicone SH-244, SH-245 or a 3:2 (by weight) mixture of SH-244 and SH-245, product of Dow Corning Toray Silicone Co., Ltd.

Preparation Process

The oil-phase components [(1), (4), (5), (7) to (11)] were heated to 80° C. to melt them. The water-phase components [(3), (6), (13), (14)], which had been heated to 80° C., were added to the above molten oil-phase components with stirring to emulsify them. The resultant emulsion was then cooled to 50° C. with stirring. The components (2), (12), (15) and (16) were then added to the emulsion, and the resultant mixture was further cooled to room temperature with stirring, thereby obtaining an O/W type cream.

Evaluation Method

A cosmetic emulsion (80 μl) was applied to hairless mice. After two hours, the mice were exposed to UV-B (1 MED or less), and just after the exposure, each of the test samples was applied. This process was conducted 3 times a week over 16 weeks. The amount of dosed energy was measured by means of a UV-Radiometer, UVR-305/365D (manufactured by TOKYO OPTICAL K.K.). The total dose was determined to be 100 mJ/cm$^2$ in an amount of energy of 0.28 mW/cm$^2$ so as to give a dose of 1 MED or less per exposure.

After completion of the application/exposure for 16 weeks, the degree of wrinkles formed was visually observed to rank the samples in accordance with the following standard (wrinkle index).

Standard (wrinkle index)

1: No wrinkle was formed;
2: Wrinkle were scarcely formed;
3: Wrinkle were somewhat formed;
4; Wrinkle were formed to a great extent.

TABLE 15

|   |   | Wrinkle index |
|---|---|---|
| Invention product | 37 | 0.7 |
|   | 38 | 0.8 |

TABLE 15-continued

| | Wrinkle index |
|---|---|
| | 39 | 0.7 |
| | 40 | 0.7 |
| | 41 | 0.8 |
| | 42 | 0.8 |
| | 43 | 0.8 |
| | 44 | 0.7 |
| | 45 | 0.8 |
| | 46 | 0.8 |
| | 47 | 0.7 |
| | 48 | 0.7 |
| | 49 | 1.0 |
| | 50 | 1.0 |
| Comparative product | 51 | 1.8 |
| | 52 | 2.0 |
| | 53 | 2.8 |
| | 54 | 2.8 |

Example 9

O/W Type Moisturizing Lotion

An O/W type moisturizing lotion having the following composition was prepared in accordance with a method known per se in the art. The thus-obtained cosmetic emulsion had excellent effects for preventing the formation of wrinkles.

| | (Composition) | (%) |
|---|---|---|
| (1) | Amide derivative (the same compound as Compound No. 37 in Table 11) | 3.0 |
| (2) | Hamamelis extract (dry solid 1.5%) | 0.5 |
| (3) | Peony extract (dry solid 1.0%) | 0.5 |
| (4) | Cetyl alcohol | 1.0 |
| (5) | Vaseline | 2.0 |
| (6) | Squalane | 5.0 |
| (7) | Dimethylpolysiloxane (6 cSt) | 2.0 |
| (8) | Glycerol | 4.0 |
| (9) | 1-(2-Hydroxyethylamino)-3-isostearyloxy-2-propanol*7 | 0.5 |
| (10) | 2-(2-Hydroxyethoxy)ethylguanidine*8 | 1.0 |
| (11) | 1,3-Butanediol | 2.0 |
| (12) | Polyoxyethylene (20) sorbitan monooleate | 0.5 |
| (13) | Sorbitan monostearate | 0.3 |
| (14) | Acid polysaccharide (the same compound as that used in Example 8) | 1.0 |
| (15) | Cholesteryl mono-n-hexadecenylsuccinate | 1.0 |
| (16) | Stearyl glycyrrhetinate | 1.0 |
| (17) | Tocopherol | 1.0 |
| (18) | Succinic acid | 0.55 |
| (19) | Sodium dihydrogenphosphate | 0.9 |
| (20) | Purified water | Balance |
| | Total | 100.0 |

*7: Prepared in accordance with Synthetic Example 3 of Japanese Patent Application Laid-open No. 17849/1995.
*8: Prepared in accordance with Example 1 of Japanese Patent Application Laid-Open No. 170628/1995.

Example 10

Sunscreen Lotion

A sunscreen lotion having the following composition was prepared in accordance with a method known per se in the art. The thus-obtained cosmetic emulsion had excellent effects for preventing the formation of wrinkles.

| | (Composition) | (%) |
|---|---|---|
| (1) | Amide derivative (the same compound as Compound No. 37 in Table 11) | 2.0 |
| (2) | Hamamelis extract (dry solid 1.5%) | 0.5 |
| (3) | Hiba arborvitae extract (dry solid 1.5%) | 0.5 |
| (4) | Octyl p-methoxycinnamate | 6.0 |
| (5) | 4-tert-Butyl-4-methoxybenzoylmethane | 2.0 |
| (6) | Oleyl oleate | 5.0 |
| (7) | Dimethylpolysiloxane (6 cSt) | 3.0 |
| (8) | Vaseline | 0.5 |
| (9) | Cetyl alcohol | 1.0 |
| (10) | Sorbitan sesquoleate | 0.8 |
| (11) | Polyoxyethylene (20) oleyl alcohol ether | 1.2 |
| (12) | 1-(2-Hydroxyethylamino)-3-(12-hydroxystearyloxy)-2-propanol | 0.4 |
| (13) | 5-Hydroxypentylguanidine | 0.8 |
| (14) | Dipropylene glycol | 6.0 |
| (15) | Acid polysaccharide (the same compound as that used in Example 8) | 1.0 |
| (16) | Ethanol | 3.0 |
| (17) | Hydroxyethylcellulose | 0.3 |
| (18) | Cholesteryl mono-n-octadecenyl succinate | 1.0 |
| (19) | Stearyl glycyrrhetinate | 1.0 |
| (20) | Tocopherol | 1.0 |
| (21) | Succinic acid | 0.2 |
| (22) | Sodium hydroxide | 0.2 |
| (23) | Purified water | Balance |
| | Total | 100.0 |

Example 11

Sunscreen Cream

A sunscreen cream having the following composition was prepared in accordance with a method known per se in the art. The thus-obtained cosmetic emulsion had excellent effects for preventing dermal aging.

| | (Composition) | (%) |
|---|---|---|
| (1) | Amide derivative (the same compound as Compound No. 37 in Table 11) | 3.0 |
| (2) | Zinc oxide coated with silicone | 7.0 |
| (3) | 2-Ethylhexyl p-methoxycinnamate | 2.0 |
| (4) | Ascorbic acid | 0.5 |
| (5) | Cholesterol | 1.0 |
| (6) | Polyether-modified silicone*3 | 2.5 |
| (7) | Methylpolysiloxane*1 | 6.0 |
| (6) | Cyclic silicone*2 | 12.0 |
| (9) | Magnesium sulfate | 0.7 |
| (10) | Acid polysaccharide (the same compound as that used in Example 8) | 1.0 |
| (11) | Allantoin | 0.1 |
| (12) | 1-(2-Hydroxyethylamino)-3-isostearyloxy-2 propanol*7 | 0.1 |
| (13) | 1-(2-Hydroxyethylamino)-3-methyloxy-2-propanol | 0.5 |
| (14) | 2-(2-Hydroxyethoxy)ethylguanidine*8 | 0.5 |
| (15) | 2-Guadinoethyl dihydrogenphosphate | 1.0 |
| (16) | Hamamelis extract (dry solid 1.5%) | 0.5 |
| (17) | Hiba arborvitae extract (dry solid 1.5%) | 0.5 |

-continued

| (Composition) | | |
|---|---|---|
| | | (%) |
| (18) | Glycerol | 3.0 |
| (19) | Antiseptic | q.s. |
| (20) | Purified water | Balance |
| | Total | 100.0 |

*1: Silicone KF96A (6 cs), product of Shin-Etsu Chemical Co., Ltd.
*2: Silicone SH-244, SH-245 or a 3:2 (by weight) mixture of SH-244 and SH-245, product of Dow Corning Toray Silicone Co., Ltd.
*3: Silicone KF-6015, product of Shin-Etsu Chemical Co., Ltd.
*7: Prepared in accordance with Synthetic Example 3 of Japanese Patent Application Laid-Open No. 17849/1995.
*8: Prepared in accordance with Example 1 of Japanese Patent Application Laid-Open No. 170628/1995.

Example 12

Hair Tonic Composition

| (Composition) | | |
|---|---|---|
| | | (%) |
| (1) | Amide derivative (the same compound as Compound No. 37 in Table 11) | 3.0 |
| (2) | Aluminum pyrrolidonecarboxylate | 0.5 |
| (3) | Ethanol | 55.0 |
| (4) | *Hiba arborvitae* extract (dry solid 1.0%) | 1.0 |
| (5) | Hamamelis extract (dry solid 1.0%) | 0.2 |
| (6) | Peony extract (dry solid 1.0%) | 0.2 |
| (7) | 1-(2-Hydroxyethylamino)-3-isostearyloxy-2-propanol*7 | 0.2 |
| (8) | 2-(2-Hydroxyethoxy)ethylguanidine*8 | 1.0 |
| (9) | Purified water | Balance |
| (10) | Perfume base | 0.3 |
| | Total | 100.0 |

*7: Prepared in accordance with synthetic Example 3 of Japanese Patent Application Laid-Open No. 17849/1995.
*8: Prepared in accordance with Example 1 of Japanese Patent Application Laid-Open No. 170628/1995.

Preparation Process

The components (1), (7) and (10) were uniformly dispersed in the component (3) under stirring. The components (2), (4) to (6), (8) and (9) were then added to the resultant dispersion, and the mixture was thoroughly stirred to prepare a suspension type hair tonic composition which had excellent retention of hairstyle set and hairstyle-setting ability, gave a pleasant feel to the hair and prevented the generation of dandruff.

Example 13

Shampoo Composition

| (Composition) | | |
|---|---|---|
| | | (%) |
| (1) | Sodium polyoxyethylene (25) lauryl ether phosphate | 15.0 |
| (2) | Coconut oil fatty acid diethanolamide | 3.0 |

-continued

| (Composition) | | |
|---|---|---|
| | | (%) |
| (3) | Amide derivative (the same compound as Compound No. 37 in Table 11) | 2.0 |
| (4) | Alkyl polyglycoside*11 | 3.5 |
| (5) | *Hiba arborvitae* extract (dry solid 1.0%) | 1.0 |
| (6) | Hamamelis extract (dry solid 1.0%) | 0.5 |
| (7) | Peony extract (dry solid 1.0%) | 0.7 |
| (8) | 1-(2-Hydroxyethylamino)-3-isostearyloxy-2 propanol*7 | 0.2 |
| (9) | 2-(2-Hydroxyethoxy)ethylguanidine*8 | 0.5 |
| (10) | Glycerol | 3.0 |
| (11) | Citric acid | 0.5 |
| (12) | Ethanol | 5.0 |
| (13) | Coloring matter | Trace amount |
| (14) | Perfume base | 0.5 |
| (15) | Purified water | Balance |
| | Total | 100.0 |

*7: Prepared in accordance with Synthetic Example 3 of Japanese Patent Application Laid-Open No. 17849/1995.
*8: Prepared in accordance with Example 1 of Japanese Patent Application Laid-Open No. 170628/1995.
*11: Dodecyl glycoside (polymerization degree of glycoside: 2)

Preparation Process

The components (3), (8) and (14) were uniformly dissolved in the component (12) at room temperature under stirring. The components (1), (2) and (15) were then added to the resultant solution and uniformly dispersed. Thereafter, the component (4) to (7), (9) to (11) and (13) were incorporated, thereby obtaining a shampoo composition which gave a pleasant feel to the hair and was uniform and stable.

Example 14

Moisturizing Essence

A moisturizing essence having the following composition was prepared in accordance with a method known per se in the art.

| (Composition) | | |
|---|---|---|
| | | (%) |
| (1) | Acid polysaccharide*6 | 0.20 |
| (2) | Xanthan gum | 0.50 |
| (3) | Ethanol | 6.40 |
| (4) | Amide derivative (the same compound as Compound No. 37 in Table 11) | 0.10 |
| (5) | 1-(2-Hydroxyethylamino)-3-isostearyloxy-2-propanol*7 | 0.20 |
| (6) | 2-(2-Hydroxyethoxy)ethylguanidine*8 | 0.10 |
| (7) | Hamamelis extract (dry solid 1.5%) | 0.50 |
| (8) | *Hiba arborvitae* extract (dry solid 1.5%) | 0.50 |
| (9) | Urea | 2.50 |
| (10) | ε-Aminocaproic acid | 0.83 |
| (11) | succinic acid | 1.50 |
| (12) | Glycerol | 12.00 |
| (13) | Dipropylene glycol | 3.00 |
| (14) | Methyl p-oxybenzoate | 0.20 |
| (15) | Polyoxyethylene isocetyl ether (20 E.O.) | 0.30 |
| (16) | Tannic acid | 0.02 |

-continued (Composition)

| | (%) |
|---|---|
| (17) Glycinebetaine | 0.50 |
| (18) Antiseptic | 0.10 |
| (19) Purified water | Balance |
| Total | 100.0 |

*6: An acid polysaccharide derived from the callus of tuberose prepared in accordance with Example 1 of Japanese Patent Application Laid-Open No. 10997/1989.
*7: Prepared in accordance with synthetic Example 3 of Japanese Patent Application Laid-Open No. 17849/1995.
*8: Prepared in accordance with Example 1 of Japanese Patent Application Laid Open No. 170628/1995.

INDUSTRIAL APPLICABILITY

The skin cosmetic compositions according to the present invention exhibit excellent water-retaining ability, and can prevent and cure skin roughness or inflammation to prevent dermal aging. The hair cosmetic compositions according to the present invention have excellent performance in protecting and maintaining the hair and head skin, and improve the feel of the hair.

This application is based on Japanese Patent Applications Nos. 7-267422, 7-327224 and 8-013917 filed on Oct. 16, 1995, Dec. 15, 1995 and Jan. 30, 1996 which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed is:

1. A cosmetic composition comprising the following components (A) and (B):

(A) at least one compound selected from amide derivatives represented by the following general formulae (1), (2), (3), and (4):

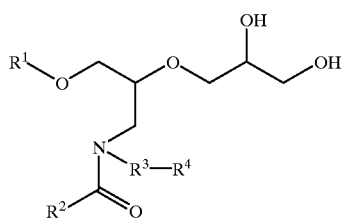

(1)

wherein $R^1$ and $R^2$ are identical to or different from each other and are, independently, a hydrocarbon group having 1 to 40 carbon atoms, which may be hydroxylated, $R^3$ is a linear or branched alkylene group having 1 to 6 carbon atoms, or a single bond, and $R^4$ is a hydrogen atom, a linear or branched alkoxyl group having 1 to 12 carbon atoms, or a 2,3-dihydroxypropyloxy group, with the proviso that when $R^3$ is a single bond, $R^4$ is a hydrogen atom;

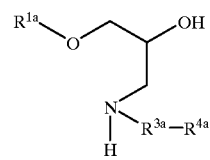

(2)

wherein $R^{1a}$ is a hydrocarbon group having 4 to 40 carbon atoms, which may be hydroxylated, $R^{3a}$ is a linear or branched alkylene group having 3 to 6 carbon atoms, and $R^{4a}$ is a linear or branched alkoxyl group having 1 to 12 carbon atoms;

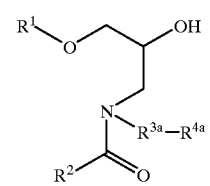

(3)

wherein $R^1$ and $R^2$ are identical to or different from each other and are, independently, a hydrocarbon group having 1 to 40 carbon atoms, which may be hydroxylated, $R^{3a}$ is a linear or branched alkylene group having 3 to 6 carbon atoms, and $R^{4a}$ is a linear or branched alkoxyl group having 1 to 12 carbon atoms;

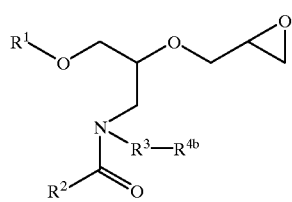

(4)

wherein $R^1$ and $R^2$ are identical with or different from each other and are, independently, a hydrocarbon group having 1 to 40 carbon atoms, which may be hydroxylated, $R^3$ is a linear or branched alkylene group having 1 to 6 carbon atoms, or a single bond, and $R^{4b}$ is a hydrogen atom, a linear or branched alkoxyl group having 1 to 12 carbon atoms, or an 2,3—epoxypropyloxy group, with the proviso that when $R^3$ is a single bond, $R^{4b}$ is a hydrogen atom; and (B) at least one component selected from the group consisting of (B-1) polyhydric alcohols, (B-2) vegetable extracts, and (B-3) organic acids or salts thereof.

2. The composition according to claim 1, wherein the component (B) comprises at least one polyhydric alcohol (B-1) and at least one organic acid or a salt thereof (B-3).

3. The composition according to claim 1, which further comprises (C) an acid hetero-polysaccharide derived from callus of a plant belonging to Polyanthes L.

4. The composition according to claim 1, which further comprises (D) a sterol.

5. The composition according to claim 1, which further comprises (E) an antiphlogistic substance.

6. The composition according to claim 1, which further comprises (F) at least one ingredient selected from the group consisting of singlet oxygen scavengers and antioxidants.

7. The composition according to claim 1, which further comprises (G) at least one ingredient selected from the group consisting of amine derivatives and acid-addition salts thereof.

8. The composition according to claim 1, which further comprises (H) at least one ingredient selected from the group consisting of guanidine derivatives and acid-addition salts thereof.

9. The composition according to claim 1, wherein said polyhydric alcohol (B-1) is selected from the group consisting of glycerol, diglycerol, triglycerol, tetraglycerol, ethylene glycol, 1,3-butylene glycol, 1,4-butylene glycol, propylene glycol, dipropylene glycol, polyethylene glycol, 1,3-propanediol, glucose, mantose, maltitol, sucrose, fructose, xylitol, sorbitol, maltotriose, threitol, erythritol, alcohols obtained by reduction of amylolytic sugar, sorbit and polyoxyalkylene alkylglucosides.

10. The composition according to claim 1, wherein said vegetable extract (B-2) is composed of a vegetable extract from at least one plant selected from the group consisting of hamamelis, peony, agrimony, Japanese catalpa, hiba arborvitae, HORUTOSO, Isodon japonicus Hara and KIJITSU.

11. The composition according to claim 1, wherein said organic acid (B-3) is selected from the group consisting of glycolic acid, lactic acid, citric acid, 2-hydroxyoctanoic acid, succinic acid, fumaric acid, maleic acid, malonic acid, 1,3propanedicarboxylic acid, stearic acid, paimitic acid, myristic acid, isostearic acid, linolic acid, linolenic acid, arachidonic acid, aspartic acid, asparagine, glycine, glutamic acid, glutamine, γ-aminobutyric acid, arginine, cysteine, alanine, dicarboxylic acid monoesters, and sterol derivatives represented by the general formula (5):

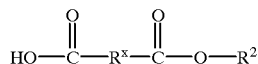

(5)

wherein $R^x$ is —$(CH_2)_l$— (l is a number of 2 to 10),

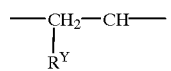

or

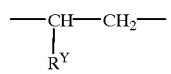

($R^Y$ is a linear or branched alkyl or alkenyl group having 6 to 20 carbon atoms), and $R^Z$ is a residue of a natural sterol or a hydrogenated product thereof in which a proton of the hydroxyl group is removed.

12. The composition according to claim 1, wherein the content of the component (A), the amide derivative, is 0.001 to 50 wt. %, based on the total weight of said composition.

13. The composition according to claim 1, wherein the content of the component (B-1), the polyhydric alcohol, is 0.01 to 50 wt. %, the content of the component (B-2), the vegetable extract, is 0.0001 to 20 wt. % in terms of dry solids, and the content of the component (B-3), the organic acid or the salt thereof, is 0.00001 to 30 wt. %, all based on the total weight of said composition.

14. The composition according to claim 3, wherein said component (C) is composed of an acid heteropolysaccharide derived from callus of tuberose, and is present in an amount of 0.0001 to 20 wt. %, based on the total weight of said composition.

15. The composition according to claim 4, wherein said component (D), the sterol, is selected from the group consisting of cholesterol alkenylsuccinates, cholesterol and cholesteryl isostearate, and is present in an amount of 0.01 to 50 wt. %, based on the total weight of said composition.

16. The composition according to claim 5, wherein said component (E), the antiphlogistic substance, is selected from the group consisting of glycyrrhetinic acid, stearyl glycyrrhetinate and ε-aminocapronic acid, and is present in an amount of 0.001 to 5 wt. %, based on the total weight of said composition.

17. The composition according to claim 6, wherein said component (F), the singlet oxygen scavenger or antioxidant, is selected from the group consisting of carotenes, tocopherols, ascorbic acid, tannic acid, epicatechin gallate, and epicarocatechin gallate, and is present in an amount of 0.001 to 5 wt. %, based on the total weight of said composition.

18. The composition according to claim 7, wherein said component (G), the amine derivative or the acid-addition salt thereof, is selected from the group consisting of 1-(2-hydroxyethylamino)-3-isostearyloxy-2-propanol, 1-(2-hydroxyethylamino)3-(12-hydroxystearyloxy)-2-propanol and 1-(2-hydroxyethylamino)-3-methyloxy-2-propanol, and is present in an amount of 0.0001 to 10 wt. %, based on the total weight of said composition.

19. The composition according to claim 8, wherein said component (H), the guanidine derivative or the acid-addition salt thereof, is selected from the group consisting of 2-(2-hydroxyethoxy)ethylguanidine, 5-hydroxypentylguanidine, 3-guanidinopropionic acid and 2-guanidinoethyl dihydrogenphosphate, and is present in am amount of 0.001 to 50 wt. %, based on the total weight of said composition.

20. The composition according to claim 1, which is a skin cosmetic composition.

21. The composition according to claim 1, which is a hair cosmetic composition.

* * * * *

UNITED STATES PATENT AND TRADEMARK OFFICE
CERTIFICATE OF CORRECTION

PATENT NO.    : 6,348,200 B1
DATED         : February 19, 2002
INVENTOR(S)   : Nakajima et al.

It is certified that error appears in the above-identified patent and that said Letters Patent is hereby corrected as shown below:

Column 51,
Line 23, "1,3propanedicarboxylic", should read -- 1,3-propanedicarboxylic --.
Line 23, "paimitic", should read -- palmitic --.

Column 52,
Line 15, (first occurrence only) of cholesterol, "cholesterol alkenylsuccinates" should read -- cholesteryl alkenylsuccinates --.

Signed and Sealed this

Third day of September, 2002

Attest:

JAMES E. ROGAN
Attesting Officer    Director of the United States Patent and Trademark Office